(12) United States Patent
Raso

(10) Patent No.: US 8,992,928 B2
(45) Date of Patent: Mar. 31, 2015

(54) ISOLATED MONOCLONAL ANTIBODY OR ANTIGEN-BINDING FRAGMENT THAT CLEAVES OCTANOYLATED NATIVE GHRELIN

(76) Inventor: Victor Raso, Brighton, MA (US)

(*) Notice: Subject to any disclaimer, the term of this patent is extended or adjusted under 35 U.S.C. 154(b) by 1536 days.

(21) Appl. No.: 12/223,852

(22) PCT Filed: Feb. 11, 2006

(86) PCT No.: PCT/US2006/005028
§ 371 (c)(1),
(2), (4) Date: May 24, 2010

(87) PCT Pub. No.: WO2007/092023
PCT Pub. Date: Aug. 16, 2007

(65) Prior Publication Data
US 2010/0254994 A1    Oct. 7, 2010

(51) Int. Cl.
*A61K 39/395* (2006.01)
*C07K 16/26* (2006.01)
*A61K 39/00* (2006.01)

(52) U.S. Cl.
CPC ............. *C07K 16/26* (2013.01); *A61K 39/0005* (2013.01); *A61K 2039/505* (2013.01); *C07K 2317/622* (2013.01)
USPC ...................................... 424/158.1; 530/300

(58) Field of Classification Search
USPC ..................................................... 424/158.1
See application file for complete search history.

(56) References Cited

U.S. PATENT DOCUMENTS

| 5,545,807 | A | * | 8/1996 | Surani et al. ..................... 800/6 |
| 6,582,945 | B1 | | 6/2003 | Raso |
| 6,872,554 | B2 | | 3/2005 | Raso |
| 2003/0211967 | A1 | | 11/2003 | Bryant et al. |
| 2004/0076645 | A1 | | 4/2004 | Bachmann et al. |
| 2011/0318300 | A1 | | 12/2011 | Bachmann et al. |

FOREIGN PATENT DOCUMENTS

| WO | WO 00/77178 A1 | | 12/2000 |
| WO | WO 01/87335 A2 | | 11/2001 |
| WO | WO 02/08250 A2 | | 1/2002 |
| WO | WO 2004/009616 | * | 1/2004 |
| WO | WO 2004/024183 A1 | | 3/2004 |
| WO | WO 2005/016951 A2 | | 2/2005 |
| WO | WO 2008/016976 A2 | | 2/2008 |

OTHER PUBLICATIONS

English et al., J. Clin Endocr. 87: 2984-2987, 2002.*
Alvarez et al., Hum. Gene Ther. 8: 229-242, 1997.*
Ahmed et al., Ghrelin: a hypothalamic GH-releasing factor in domestic fowl (*Gallus domesticus*). J Endocrinol. Jan. 2002;172(1):117-25.
Banks et al., Extent and direction of ghrelin transport across the blood-brain barrier is determined by its unique primary structure. J Pharmacol Exp Ther. Aug. 2002;302(2):822-7.
Bednarek et al., Structure-function studies on the new growth hormone-releasing peptide, ghrelin: minimal sequence of ghrelin necessary for activation of growth hormone secretagogue receptor 1a. J Med Chem. Nov. 16, 2000;43(23):4370-6.
Blackburn et al., Catalytic antibodies for the hydrolysis of unactivated peptides. Biochem Soc Trans. Nov. 1993;21(4):1102-7.
Cummings et al., A preprandial rise in plasma ghrelin levels suggests a role in meal initiation in humans. Diabetes. Aug. 2001;50(8):1714-9.
Cummings et al., Plasma ghrelin levels after diet-induced weight loss or gastric bypass surgery. N Engl J Med. May 23, 2002;346(21):1623-30.
De Vriese et al., Ghrelin degradation by serum and tissue homogenates: identification of the cleavage sites. Endocrinology. Nov. 2004;145(11):4997-5005. Epub Jul. 15, 2004.
Frenkel et al., N-terminal EFRH sequence of Alzheimer's beta-amyloid peptide represents the epitope of its anti-aggregating antibodies. J Neuroimmunol. Aug. 1, 1998;88(1-2):85-90.
Gaytan et al., Immunolocalization of ghrelin and its functional receptor, the type 1a growth hormone secretagogue receptor, in the cyclic human ovary. J Clin Endocrinol Metab. Feb. 2003;88(2):879-87.
Hanson et al., Catalytic antibodies and their applications. Curr Opin Biotechnol. Dec. 2005;16(6):631-6. Epub Oct. 21, 2005.
Haqq et al., Serum ghrelin levels are inversely correlated with body mass index, age, and insulin concentrations in normal children and are markedly increased in Prader-Willi syndrome. J Clin Endocrinol Metab. Jan. 2003;88(1):174-8.
Hosoda et al., Structural divergence of human ghrelin. Identification of multiple ghrelin-derived molecules produced by post-translational processing. J Biol Chem. Jan. 3, 2003;278(1):64-70. Epub Oct. 31, 2002.
Kerchner et al., Bapineuzumab. Expert Opin Biol Ther. Jul. 2010;10(7):1121-30.
Kojima et al., Ghrelin: structure and function. Physiol Rev. Apr. 2005;85(2):495-522.
Kojima et al., Ghrelin is a growth-hormone-releasing acylated peptide from stomach. Nature. Dec. 9, 1999;402(6762):656-60.
Landry et al., Antibody-catalyzed degradation of cocaine. Science. Mar. 26, 1993;259(5103):1899-901.
Lerner et al., At the crossroads of chemistry and immunology: catalytic antibodies. Science. May 3, 1991;252(5006):659-67.

(Continued)

*Primary Examiner* — Gyan Chandra
(74) *Attorney, Agent, or Firm* — Wolf, Greenfield & Sacks, P.C.

(57) ABSTRACT

The present invention relates, in part, to agents for binding and/or inactivating native ghrelin. These agents include those that specifically bind and/or cleave octanoylated native ghrelin. Such agents include antibodies and enzymes. The agents also include those that can be used to generate antibodies that specifically bind and/or cleave octanoylated native ghrelin. Compositions that include the agents are also provided. Further provided are methods of producing and using the agents and compositions thereof. For instance, the agents and compositions can be used to reduce or eliminate the hunger response activity of octanoylated native ghrelin. Therefore, the agents, compositions and methods provided can be used to suppress appetite and/or treat obesity. In addition, the agents, compositions and methods can be used to treat any disease associated with or caused by ghrelin (e.g., Prader-Willi Syndrome).

12 Claims, 12 Drawing Sheets

(56) References Cited

OTHER PUBLICATIONS

Moller et al., Splanchnic release of ghrelin in humans. J Clin Endocrinol Metab. Feb. 2003;88(2):850-2.

Mun et al., Current status of medical and surgical therapy for obesity. Gastroenterology. Feb. 2001;120(3):669-81.

Murakami et al., Role for central ghrelin in food intake and secretion profile of stomach ghrelin in rats. J Endocrinol. Aug. 2002;174(2):283-8.

Nakazato et al., A role for ghrelin in the central regulation of feeding. Nature. Jan. 11, 2001;409(6817):194-8.

Patterson et al., Characterization of ghrelin-like immunoreactivity in human plasma. J Clin Endocrinol Metab. Apr. 2005;90(4):2205-11. Epub Jan. 18, 2005.

Smith et al., Prolonged in vivo residence times of antibody fragments associated with albumin. Bioconjug Chem. Sep.-Oct. 2001;12(5):750-6.

Solomon et al., Disaggregation of Alzheimer beta-amyloid by site-directed mAb. Proc Natl Acad Sci U S A. Apr. 15, 1997;94(8):4109-12.

Solomon et al., Monoclonal antibodies inhibit in vitro fibrillar aggregation of the Alzheimer beta-amyloid peptide. Proc Natl Acad Sci U S A. Jan. 9, 1996;93(1):452-5.

Sun et al., Deletion of ghrelin impairs neither growth nor appetite. Mol Cell Biol. Nov. 2003;23(22):7973-81.

Tanaka, Catalytic antibodies as designer proteases and esterases. Chem Rev. Dec. 2002;102(12):4885-906.

Tanaka et al., Ghrelin is involved in the decidualization of human endometrial stromal cells. J Clin Endocrinol Metab. May 2003;88(5):2335-40.

Wang et al., Peripheral ghrelin selectively increases Fos expression in neuropeptide Y—synthesizing neurons in mouse hypothalamic arcuate nucleus. Neurosci Lett. May 31, 2002;325(1):47-51.

Wortley et al., Genetic deletion of ghrelin does not decrease food intake but influences metabolic fuel preference. Proc Natl Acad Sci U S A. May 25, 2004;101(21):8227-32. Epub May 17, 2004.

Xu et al., Catalytic antibodies: hapten design strategies and screening methods. Bioorg Med Chem. Oct. 15, 2004;12(20):5247-68.

Zigman et al., In search of an effective obesity treatment: a shot in the dark or a shot in the arm? Proc Natl Acad Sci U S A. Aug. 29, 2006;103(35):12961-2. Epub Aug. 21, 2006. Erratum in: Proc Natl Acad Sci U S A. Oct. 3, 2006;103(40):14977.

\* cited by examiner

ISOLATED MONOCLONAL ANTIBODY OR ANTIGEN-BINDING FRAGMENT THAT CLEAVES OCTANOYLATED NATIVE GHRELIN

GOVERNMENT SUPPORT

Aspects of the invention may have been made using funding from National Institutes of Health Grant number AG 17658. Accordingly, the Government may have rights in the invention.

FIELD OF THE INVENTION

The present invention relates, in part, to agents for binding and/or inactivating native ghrelin. These agents include those that specifically bind and/or cleave octanoylated native ghrelin (e.g., antibodies, enzymes, etc.). The agents provided also include those that generate antibodies that specifically bind and/or cleave octanoylated native ghrelin. The invention further relates, in part, to compositions that include the agents provided as well as methods of producing and using the agents and compositions thereof.

BACKGROUND OF THE INVENTION

In the United States approximately 61 million people or 30 percent of the adult population are classified as obese (body mass index >30). Morbidly obese (body mass index >40) Americans comprise 5 percent of the adult population (Flegal, K. M., et al. 2002. *Jama* 288:1723-1727.) Having reached epidemic proportions, obesity adversely impacts our national health, health care costs and reduces life expectancy. This condition also is personally devastating in terms of the resulting stigma and widespread discrimination that occur. Sadly about 15 percent of children are overweight or obese and, as a result, many will develop serious diseases later in life. These ancillary health conditions can include hypertension, type 2 diabetes, heart disease, stroke, cancer and additional medical problems.

SUMMARY OF THE INVENTION

This invention is based, in part, on the discovery of certain agents that specifically bind and/or cleave octanoylated native ghrelin. The invention is also based, in part, on the discovery of agents, such as ghrelin transition state analogs, that can be used to generate antibodies that specifically bind and/or cleave octanoylated native ghrelin. This invention is further based, in part, on the discovery that some of these agents can result in the inactivation of octanoylated native ghrelin and can be used for reducing or eliminating an activity of octanoylated native ghrelin, such as its hunger response activity. It has also been found that these agents can be used to reduce or eliminate appetite in a subject, to treat a subject with a condition or disorder associated with or caused by ghrelin production, etc. The agents provided, therefore, can be used to treat or prevent obesity in a subject. The agents provided can also be used to treat Prader-Willi Syndrome (PWS).

In one aspect of the invention a composition is provided that comprises a ghrelin transition state analog. The ghrelin transition state analog in one embodiment is one that mimics the tetrahedral intermediate of octyl ester hydrolysis of octanoylated native ghrelin. In another embodiment the ghrelin transition state analog mimics the tetrahedral intermediate formed during peptide hydrolysis of native ghrelin. In one embodiment the composition further comprises an adjuvant. In another embodiment the adjuvant is complete Freunds adjuvant or incomplete Freunds adjuvant. In yet another embodiment the composition further comprises a pharmaceutically acceptable carrier. The compositions provided can be used to generate antibodies that bind and/or cleave octanoylated native ghrelin. In one embodiment antibodies are generated that specifically bind octanoylated native ghrelin. In another embodiment antibodies are generated that inactivate octanoylated native ghrelin. In one embodiment the inactivation is a result of binding to octanoylated native ghrelin. In another embodiment the inactivation is a result of cleavage of octanoylated native ghrelin.

In still another embodiment the ghrelin transition state analog comprises a compound of Formula 1.

$$N_1N_2X_1N_3N_4 \qquad \text{(Formula 1)}$$

in which
$N_1$ is glycine;
$N_2$ is serine;
$X_1$ is

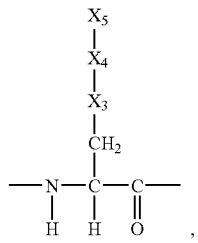

wherein $X_3$ is O or NH, $X_4$ is O=S=O or O=P—OH and $X_5$ is a hydrophobic moiety,
$N_3$ is phenylalanine; and
$N_4$ is leucine;
and wherein $N_1$ and $N_4$ each may be present or absent.

In one embodiment the hydrophobic moiety is an alkyl chain, aliphatic acid or aromatic acid. In another embodiment the alkyl chain is a $C_6$, $C_7$, $C_8$, $C_9$ or $C_{10}$ alkyl chain. In yet another embodiment the hydrophobic moiety is benzene or a 1-adamantaneacetyl group. In still a further embodiment the ghrelin transition state analog comprises the 28 amino acid sequence of native ghrelin, or any portion thereof that contains at least one serine, wherein a serine is modified with one of the octyl ester analogs shown as molecules 8-11 of FIG. 17. In one embodiment the ghrelin transition state analog comprises a portion of the 28 amino acid sequence of native ghrelin that includes the first two serines residues of the native sequence, and the second serine is the one that is modified.

In a further embodiment the ghrelin transition state analog comprises at least 3 or more consecutive amino acids of SEQ ID NO: 1 or a conservatively substituted version thereof, wherein at least one of the peptide bonds (i.e., —CO—NH—) has been replaced with a statyl moiety (i.e., —CHOH—CH$_2$—CO—NH—) or a reduced peptide bond (i.e., —CH$_2$—NH$_2^+$—). In one embodiment the peptide bond that is replaced is at or near the N-terminal portion of the amino acid sequence.

In another aspect of the invention antibodies or antigen-binding fragments thereof are provided that are produced by administering the agents or compositions provided. In one embodiment a transition state analog or composition thereof is administered to a subject. In another embodiment an adjuvant is also administered to the subject. In still another aspect of the invention compositions of the antibodies or antigen-binding fragments thereof and a pharmaceutically acceptable carrier are provided. In one embodiment the compositions further comprise an additional therapeutic agent.

In still another aspect of the invention a composition is provided that comprises an antibody or antigen-binding fragment thereof that specifically binds octanoylated native ghrelin. In one embodiment the composition further comprises a pharmaceutically acceptable carrier. In another embodiment the composition can further comprise an additional therapeutic agent. In another aspect of the invention a pharmaceutical preparation comprising an antibody or antigen-binding fragment thereof that specifically binds octanoylated native ghrelin is provided. In one embodiment the antibody or antigen-binding fragment thereof is in an amount effective to eliminate or reduce the hunger response activity of octanoylated native ghrelin. In another embodiment the antibody or antigen-binding fragment thereof is a monoclonal antibody. In yet another embodiment the antibody or antigen-binding fragment thereof is a single chain Fv (scFv) antibody. In a further embodiment the antibody or antigen-binding fragment thereof is conjugated to an agent that prolongs its residence in the body. In one embodiment the antibody or antigen-binding fragment thereof is conjugated to polyethylene glycol (PEG), albumin or an albumin-binding peptide.

In still another aspect of the invention a composition is provided that comprises an antibody or antigen-binding fragment thereof that cleaves octanoylated native ghrelin. In one embodiment the composition further comprises a pharmaceutically acceptable carrier. In another embodiment the composition can further comprise an additional therapeutic agent. In another aspect of the invention a pharmaceutical preparation of an antibody or antigen-binding fragment thereof that cleaves octanoylated native ghrelin is also provided. In one embodiment the antibody or antigen-binding fragment thereof is in an amount effective to eliminate or reduce the hunger response activity of octanoylated native ghrelin. In another embodiment the antibody or antigen-binding fragment thereof is a monoclonal antibody. In still another embodiment the antibody or antigen-binding fragment is a scFv. In a further embodiment the antibody or antigen-binding fragment thereof is conjugated to an agent that prolongs its residence in the body. In one embodiment the antibody or antigen-binding fragment thereof is conjugated to polyethylene glycol (PEG), albumin or an albumin-binding peptide.

In another aspect of the invention uses of the compositions and preparations provided for the preparation of a medicament are also provided. In one embodiment the medicament is for reducing or eliminating the hunger response activity of octanoylated native ghrelin. In another embodiment the medicament is for suppressing appetite. In yet another embodiment the medicament is for treating or preventing a condition or disorder associated with or caused by octanoylated native ghrelin. In a further embodiment the medicament is for treating or preventing obesity. In still a further embodiment the medicament is for treating PWS.

In yet another aspect of the invention a method of generating anti-ghrelin antibodies is provided. The method includes the step of administering a composition comprising a ghrelin transition state analog to a subject in an amount effective to generate anti-ghrelin antibodies. In one embodiment the method further comprises administering an adjuvant to the subject. The adjuvant can be administered prior to, subsequent to or concomitantly with the composition. In still another embodiment the method further comprises administering one or more booster doses of a ghrelin antigen. In one embodiment the ghrelin antigen is octanoylated native ghrelin or a ghrelin transition state analog. In another embodiment the ghrelin antigen is an analog as shown in Formula 2. In still another embodiment the method further comprises selecting anti-ghrelin antibodies that selectively bind octanoylated native ghrelin. In yet another embodiment the method further comprises selecting anti-ghrelin antibodies that cleave octanoylated native ghrelin. In a further embodiment the anti-ghrelin antibodies bind and then cleave octanoylated native ghrelin.

In a further aspect of the invention a method of generating anti-ghrelin antibodies is provided, wherein the method includes the steps of administering a ghrelin antigen to a subject in an amount effective to generate anti-ghrelin antibodies, and selecting anti-ghrelin antibodies that specifically bind octanoylated native ghrelin or cleave octanoylated native ghrelin. In one embodiment the ghrelin antigen is octanoylated ghrelin. In another embodiment the octanoylated ghrelin is octanoylated native ghrelin. In yet another embodiment the ghrelin antigen is an analog as shown in Formula 2. In still another embodiment the ghrelin antigen is a ghrelin transition state analog. In another embodiment the method further comprises administering an adjuvant to the subject. In still another embodiment the method further comprises administering one or more booster doses of a ghrelin antigen.

In yet another aspect of the invention a method of eliminating or reducing an activity of octanoylated native ghrelin is provided. In one embodiment the activity of octanoylated native ghrelin is its hunger response activity. The method includes the step of administering to a subject an octanoylated native ghrelin inactivating agent in an amount effective to eliminate or reduce the activity of octanoylated native ghrelin. In one embodiment the octanoylated native ghrelin inactivating agent is an agent that specifically binds and reduces or eliminates an activity of octanoylated native ghrelin. In another embodiment the octanoylated native ghrelin inactivating agent is an agent that cleaves and reduces or eliminates an activity of octanoylated native ghrelin. In one embodiment the octanoylated native ghrelin inactivating agent is an antibody or antigen-binding fragment thereof. In another embodiment the octanoylated native ghrelin inactivating agent is an enzyme. In one embodiment the enzyme is a butyryl cholinesterase or carboxylesterase. In another embodiment the octanoylated native ghrelin inactivating agent is an agent that generates anti-ghrelin antibodies that reduce or eliminate an activity of octanoylated native ghrelin (e.g., by cleaving or specifically binding octanoylated native ghrelin). In one embodiment the composition is administered in an amount effective to suppress appetite in the subject. In another embodiment the composition is administered in an amount effective to treat obesity. In yet another embodiment the subject has PWS, and the composition is administered in an amount effective to treat PWS.

In still a further aspect of the invention a method of eliminating or reducing an activity of octanoylated native ghrelin is provided, wherein the method includes administering to a subject, in an amount effective to eliminate or reduce the activity of octanoylated native ghrelin, a composition comprising a ghrelin transition state analog. In one embodiment the activity of octanoylated native ghrelin is its hunger response activity. In another embodiment the ghrelin transition state analog is a compound as provided in Formula 1. In one embodiment the hydrophobic moiety is an alkyl chain, aliphatic acid, or aromatic acid. In another embodiment the hydrophobic moiety is a benzene or a 1-adamantaneacetyl group. In another embodiment the alkyl chain is a $C_6$, $C_7$, $C_8$, $C_9$ or $C_{10}$ alkyl chain. In still a further embodiment the ghrelin transition state analog comprises the 28 amino acid sequence of native ghrelin, or any portion thereof that contains at least one serine, wherein a serine is modified with one of the octyl ester analogs shown as molecules 8-11 of FIG. 17. In one embodiment the ghrelin transition state analog comprises a portion of the 28 amino acid sequence of native ghrelin that includes the first two serines residues of the native sequence, and the second serine is the one that is modified. In another embodiment the method further comprises administering an adjuvant to the subject. In still another embodiment the adjuvant is administered prior to, subsequent to or concomitantly with the composition. In yet another embodiment the method further comprises administering one or more booster doses of a ghrelin antigen. In one embodiment the ghrelin antigen is octanoylated native ghrelin, a ghrelin transition state analog or an analog as shown in Formula 2. In yet a further embodiment the composition is administered in an amount effective to suppress appetite in the subject. In another embodiment the composition is administered in an amount effective to treat obesity. In still another embodiment the subject has PWS, and the composition is administered in an amount effective to treat PWS.

In a further aspect of the invention a method of screening is provided. In one embodiment the method includes contacting a candidate agent with a composition comprising an octanoylated ghrelin, ghrelin transition state analog or an analog as shown in Formula 2, and determining whether the candidate agent binds and/or cleaves the composition. In one embodiment the octanoylated ghrelin is octanoylated native ghrelin. In another embodiment the candidate agent is a candidate ghrelin inactivating agent and the method further comprises the step of determining the reduction or elimination of an activity of native ghrelin (e.g., octanoylated native ghrelin). In one embodiment the activity is the hunger response activity of octanoylated native ghrelin. In another embodiment the candidate agent or candidate ghrelin inactivating agent is an antibody or antigen-binding fragment thereof. In one embodiment the antibody or antigen-binding fragment thereof is a monoclonal or scFv antibody. In another embodiment the candidate agent or candidate ghrelin inactivating agent is an enzyme. In one embodiment the candidate agent or candidate ghrelin inactivating agent is labeled. In another embodiment the label is biotin or a fluorescent label.

Any of the compositions or preparations provided can further comprise a pharmaceutically acceptable carrier. In another embodiment the compositions or preparations provided further comprise an additional therapeutic agent, such as a therapeutic agent for suppressing appetite or treating obesity. In still another embodiment the compositions or preparations provided further comprise an adjuvant. In one embodiment the adjuvant is complete Freunds adjuvant or incomplete Freunds adjuvant.

In some embodiments where passage of the agents through the blood brain barrier is desired, the agents or compositions provided can be administered intravenously. In other embodiments where administration to the vagus nerve is desired the agents or compositions provided are administered intraperitoneally.

In another embodiment where passage across the blood brain barrier is desired tha antibodies or antigen-binding fragments are coupled to a ligand, such as an antibody, that is trancytosed through the brain capillary endothelial cells. In one embodiment the ligand can bind a receptor present on the blood brain barrier. Such receptors include the transferrin receptor or insulin receptor. Therefore, the ligand can be an antibody to the transferrin receptor or insulin receptor.

Each of the limitations of the invention can encompass various embodiments of the invention. It is, therefore, anticipated that each of the limitations of the invention involving any one element or combinations of elements can be included in each aspect of the invention.

DESCRIPTION OF THE INVENTION

Active ghrelin is an octanoylated, 28 amino acid peptide hormone produced chiefly in the stomach (Kojima, M., et al. 1999. *Nature* 402:656-660.) Ghrelin that is produced by the empty stomach quickly passes into the blood stream and then to the brain and/or vagus nerve where it stimulates hunger. Compositions and methods are provided herein that comprise agents that inactivate the hunger response activity of ghrelin. Such agents in some embodiments specifically bind and/or cleave ghrelin. In other embodiments such agents result in the production of antibodies that specifically bind and/or cleave ghrelin. The agents and compositions provided herein can be used to suppress appetite and/or treat obesity, and methods to do so are also provided.

Figure 1:
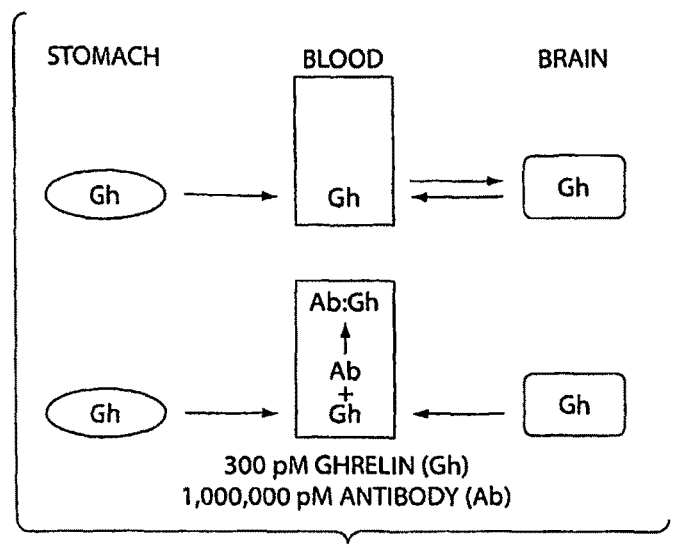
FIG. 1 provides a diagram of the ghrelin pathway.
Figure 2:
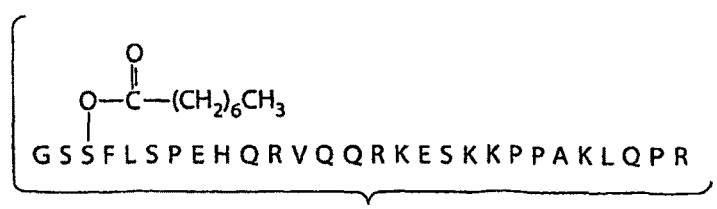
FIG. 2 provides the structure including the amino acid sequence of human octanoylated native ghrelin.

The agents provided in some embodiments specifically bind and/or cleave native ghrelin. As used herein, "native ghrelin" refers to a ghrelin peptide that is produced endogenously in a subject. The term is intended to encompass active and inactive forms. For instance, in humans, the active form of ghrelin is octanoylated on the second serine of its 28 amino acid backbone, the structure of which is provided in FIG. 2. "Native ghrelin" is intended to include this form of human ghrelin. It is also intended to encompass the inactive, non-octanoylated form. As used herein, "octanoylated native ghrelin" is intended to refer to the octanoylated form of native ghrelin as shown in FIG. 2, which contains an octyl ester on the second serine of the amino acid sequence. "Octanoylated ghrelin", however, is intended to refer to any ghrelin peptide, including a native ghrelin or a fragment thereof, which contains an octyl ester moiety. Preferably, the octanoylated ghrelin contains a N-terminal portion of the native 28 amino acid sequence with a serine residue and an octyl ester moiety on this serine residue. More preferably, the octanoylated ghrelin contains a N-terminal portion of the native 28 amino acid sequence with two serine residues and an octyl ester moiety on the second serine residue. "Non-octanoylated ghrelin" refers to any ghrelin peptide, the complete native 28 amino acid sequence or fragment thereof, which does not contain an octyl ester moiety.

The agents that specifically bind and/or cleave native ghrelin include antibodies (also referred to herein as "anti-ghrelin antibodies".) Anti-ghrelin antibodies in some embodiments are antibodies that specifically bind and/or cleave octanoylated native ghrelin. As used herein, "specifically binds" refers to the preferential binding of the antibody to ghrelin or a particular kind or group of ghrelins over other antigens. In some embodiments the other antigens are other endogenous antigens only. "Preferential" refers to an increased affinity for ghrelin or the particular kind or group of ghrelins over other antigens. For instance, when the antibody is an antibody that specifically binds octanoylated ghrelin, the antibody binds preferentially to octanoylated ghrelin, preferentially recognizing ghrelins with an octyl ester. As another example, an antibody that specifically binds octanoylated native ghrelin is an antibody that binds preferentially to octanoylated native ghrelin, preferentially recognizing this particular form of ghrelin over other forms of ghrelin and non-ghrelin antigens. The antibody that specifically binds octanoylated ghrelin, such as octanoylated native ghrelin, therefore, can typically bind with an affinity that is at least 25%, 50%, 100%, 150%, 200%, 300%, 400%, 500% or greater than its affinity for binding to non-octanoylated ghrelin or other antigens. The antibodies provided can, in some embodiments, have an association constant of about $1\times10^4 M^{-1}$, $1\times10^5 M^{-1}$, $1\times10^6 M^{-1}$, $5\times10^6 M^{-1}$, $1\times10^7 M^{-1}$, $5\times10^7 M^{-1}$, $1\times10^8 M^{-1}$, $2\times10^8 M^{-1}$, $5\times10^8 M^{-1}$, $7.5\times10^8 M^{-1}$, $1\times10^9 M^{-1}$, $2\times10^9 M^{-1}$, $5\times10^9 M^{-1}$, $7.5\times10^9 M^{-1}$ or $1\times10^{10} M^{-1}$. In one embodiment the antibodies provided have an association constant of at least $1\times10^6 M^{-1}$, $1\times10^7 M^{-1}$, $1\times10^8 M^{-1}$, $1\times10^9 M^{-1}$ or $1\times10^{10} M^{-1}$.

Anti-ghrelin antibodies include antibodies that specifically bind octanoylated native ghrelin and, preferably, inactivate it. The antibodies can inactivate the protein by binding octanoylated native ghrelin and restricting it's ability to cross the blood brain barrier. Alternatively, the antibodies can bind octanoylated native ghrelin and disrupt its stimulation of the vagus nerve. Anti-ghrelin antibodies also include antibodies that cleave native ghrelin and, preferably, inactivate it. Antibodies that cleave and inactivate octanoylated native ghrelin can do so by cleaving the octyl ester and/or the amino acid backbone of the active form of the protein. In some embodiments the antibodies cleave at or near the N-terminal portion of native ghrelin. In other embodiments the antibodies cleave between residues 1 and 2, 2 and 3, 3 and 4, 4 and 5, 5 and 6, 6 and 7, 7 and 8, 8 and 9 or 9 and 10 of the amino acid sequence of native ghrelin. In some embodiments, therefore, the antibodies are selected for their ability to specifically bind, cleave or inactivate octanoylated native ghrelin or some combination thereof. Additionally, in some embodiments the antibodies are selected for where they cleave native ghrelin.

Control and inhibitor studies can be used to show that ghrelin catalysis (i.e., cleavage) is not due to endogenous esterases that might have been purified along with an antibody. The main esterases that might contaminate the purified antibody preparations are carboxylesterase or butylcholinesterase (De Vriese, C., et al. *Endocrinology.* 2004 November; 145(11):4997-5005) and a variety of inhibitors that selectively inhibit each of these enzymes are available. A $^{125}$I-labeled $G_{1-28}$ probe is available comercially and can be tested as a substrate in this assay. In addition, the phosphonate transition state analog, $G_{1-5}P$, is not hydrolysable and can serve as a potent inhibitor of antibody-mediated cleavage of ghrelin.

As used herein, the term "antibody" refers to glycoproteins comprising at least two heavy (H) chains and two light (L) chains inter-connected by disulfide bonds. Each heavy chain is comprised of a heavy chain variable region (abbreviated herein as HCVR or $V_H$) and a heavy chain constant region. The heavy chain constant region is comprised of three domains, $C_H1$, $C_H2$ and $C_H3$. Each light chain is comprised of a light chain variable region (abbreviated herein as LCVR or $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The term "antibody" is also intended to include antigen-binding fragments of the antibodies. The term "antigen-binding fragment" as used herein, refers to one or more portions of an antibody that retain the ability to specifically bind to an antigen (e.g., octanoylated native ghrelin). Examples of binding fragments encompassed within the term "antigen-binding fragment" of an antibody include (i) a Fab fragment, a monovalent fragment consisting of the $V_L$, $V_H$, $C_L$ and $C_H1$ domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) *Nature* 341:544-546) which consists of a $V_H$ domain; and (vi) an isolated complementarity determining region (CDR). These antibody fragments are obtained using conventional procedures, such as proteolytic fragmentation procedures, as described in J. Goding, Monoclonal Antibodies: Principles and Practice, pp 98-118 (N.Y. Academic Press 1983), which is hereby incorporated by reference, as well as by other techniques known to those with skill in the art. The fragments are screened for utility in the same manner as are intact antibodies.

The antibodies can be isolated antibodies. An "isolated antibody" refers to an antibody which is substantially free of other antibodies having different antigenic specificities (e.g., an isolated antibody that specifically binds to octanoylated native ghrelin is substantially free of antibodies that specifically bind antigens other than octanoylated native ghrelin, the other antigens include other forms of ghrelin). An isolated antibody that specifically binds to an epitope, isoform or variant of native ghrelin may, however, have cross-reactivity to other ghrelin forms, analogs or related antigens, e.g., from other species (e.g., native ghrelin species homologs). Moreover, an isolated antibody may be substantially free of other cellular material and/or chemicals. In some embodiments, however, the isolated antibody specifically binds to an epitope of octanoylated native ghrelin and does so with a specificity such that there is little to no cross-reactivity with non-octanoylated native ghrelin.

The isolated antibodies of the invention encompass various antibody isotypes, such as IgG1, IgG2, IgG3, IgG4, IgM, IgA1, IgA2, IgAsec, IgD, IgE. As used herein, "isotype" refers to the antibody class (e.g., IgM or IgG1) that is encoded by heavy chain constant region genes. The antibodies can be full length or can include only an antigen-binding fragment such as the antibody constant and/or variable domain of IgG1, IgG2, IgG3, IgG4, IgM, IgA 1, IgA2, IgAsec, IgD or IgE or could consist of a Fab fragment, a F(ab')$_2$ fragment, and a Fv fragment.

The antibodies can be single chain antibodies (scFvs), comprising linked $V_H$ and $V_L$ domains and which retain the conformation and specific binding activity of the native idiotype of the antibody. With scFv antibodies any adverse inflammatory response can be circumvented because the scFv antibodies cannot form immune aggregates and do not activate the cells which cause inflammation. ScFv antibodies possess no Fc region for the activation of immune complement or microglial cells and macrophages. ScFv antibodies can also be advantageous for passaging into the central nervous system (CNS). By passaging into the CNS, scFv antibodies can be used to inactivate ghrelin beyond sequestering native ghrelin in the blood. In addition, since the reactivity of an anti-ghrelin scFv is directed against a single epitope on ghrelin, precise regions of ghrelin can be targeted.

Single chain antibodies are well known in the art and can be produced by standard methods (See, e.g., Alvarez et al., *Hum. Gene Ther.* 8: 229-242 (1997)). For example, recombinant methods can be used to generate scFvs, and such scFvs, can consist of a $V_L$ and $V_H$ joined by a synthetic peptide linker. The scFv antibodies can also be obtained as an antigen binding fragment of an antibody. In addition, scFv antibodies can be identified by screening a library with one or more ghrelin peptides/antigens. For example, a nonimmune library of $10^9$ different human antibody scFv fragments has been cloned and expressed on the surface of yeast (Feldhaus, M. J., et al. 2003. *Nature Biotech*. advanced online publication.) The pPNL6 vector containing the scFv library can be specifically designed to display human scFv antibodies with C-terminal HA and N-terminal c-myc epitope tags on the surface of *S. cerevisiae*. The extracellular surface display of scFv and epitope tags allow for the detection of antigen-antibody interactions by flow cytometry (Feldhaus, M. J., et al. 2003. *Nature Biotech*. advanced online publication.) As a eukaryote, *S. cerevisiae* offers the advantage of post-translational modifications and processing of mammalian proteins. Therefore, displayed anti-ghrelin scFv antibodies will be close to their native form. In addition, the short doubling time of *S. cerevisiae* will allow for the rapid analysis and isolation of ghrelin-specific scFv antibodies, particularly human scFv antibodies. Molecular interactions with the scFv antibody expressed on the yeast can be easily assayed after incubating the cells with select ghrelin peptides/antigens. The screening process used for enriching and identifying ghrelin-specific binders within the scFv library employs a combination of two rounds of selection with magnetic particles followed by three rounds of flow cytometric sorting. The anti-ghrelin scFv molecules can be expressed in yeast and secreted as 25-40 kDa monovalent molecules that can be affinity purified via a 6-His tag.

Such a screening has been performed, and anti-ghrelin scFv antibodies have been prepared (clones G1, G11 and G14). The G1 scFv bound to two octanoylated forms (G1-5 octanoylated and full-length octanoylated ghrelin) but not to a peptide without an octyl ester. Thus, the ghrelin epitope that G1 recognizes is proximal to its amino terminus and involves the octyl ester moiety at the second serine. In addition, the three scFv antibodies resulted in a reduction of initial food intake in mice. Compositions of and methods of using scFv antibodies that specifically bind octanoylated ghrelin (e.g., octanoylated native ghrelin) and/or inactivate native ghrelin are provided herein.

The antibodies of the present invention can also be polyclonal, monoclonal, or a mixture of polyclonal and monoclonal antibodies. The antibodies can be produced by a variety of techniques. Procedures for raising polyclonal and monoclonal antibodies are well known in the art. A procedure for producing monoclonal anti-ghrelin antibodies is also provided in the Examples. The term "monoclonal antibody", as used herein, refers to a preparation of antibody molecules of single molecular composition. A monoclonal antibody displays a single binding specificity and affinity for a particular epitope.

In other embodiments, the antibodies can be recombinant antibodies. The term "recombinant antibody", as used herein, is intended to include antibodies that are prepared, expressed, created or isolated by recombinant means, such as antibodies isolated from an animal (e.g., a mouse) that is transgenic for another species' immunoglobulin genes, antibodies expressed using a recombinant expression vector transfected into a host cell, antibodies isolated from a recombinant, combinatorial antibody library, or antibodies prepared, expressed, created or isolated by any other means that involves splicing of immunoglobulin gene sequences to other DNA sequences.

In yet other embodiments, the antibodies can be chimeric or humanized antibodies. As used herein, the term "chimeric antibody" refers to an antibody, that combines the murine variable or hypervariable regions with the human constant region or constant and variable framework regions. As used herein, the term "humanized antibody" refers to an antibody that retains only the antigen-binding CDRs from the parent antibody in association with human framework regions (see, Waldmann, 1991, *Science* 252:1657). Such chimeric or humanized antibodies retaining binding specificity of a murine antibody are expected to have reduced immunogenicity when administered in vivo for diagnostic, prophylactic or therapeutic applications.

In certain embodiments, the antibodies are human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse have been grafted onto human framework sequences (referred to herein as "humanized antibodies").

Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference. These animals have been genetically modified such that there is a functional deletion in the production of endogenous (e.g., murine) antibodies. The animals are further modified to contain all or a portion of the human germ-line immunoglobulin gene locus such that immunization of these animals results in the production of fully human antibodies to the antigen of interest. Following immunization of these mice (e.g., XenoMouse (Abgenix), HuMAb mice (Medarex/GenPharm)), monoclonal antibodies are prepared according to standard hybridoma technology. These monoclonal antibodies have human immunoglobulin amino acid sequences and therefore will not provoke human anti-mouse antibody (HAMA) responses when administered to humans.

The antibodies provided herein can be produced with any ghrelin antigen that generates antibodies that specifically bind and/or cleave octanoylated native ghrelin. Preferably the antibodies inactivate an activity of octanoylated native ghrelin (e.g., its hunger response activity). As used herein, "ghrelin antigens" include native ghrelin (e.g., octanoylated native ghrelin), fragments of native ghrelin, such as that contain the octyl ester of the octanoylated native form, and analogs of native ghrelin and its fragments. Analogs of native ghrelin and its fragments include compositions comprising a compound with the following formula (Formula 2):

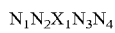

in which
N$_1$ is glycine,
N$_2$ is serine,
X$_1$ is

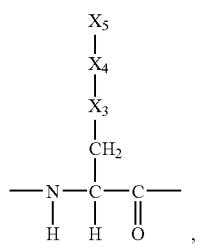

wherein X$_3$ is O, NH or S; X$_4$ is C=O when X$_3$ is NH or S, S=O when X$_3$ is O, or S when X$_3$ is O or NH; and X$_5$ is a hydrophobic moiety;
N$_3$ is phenylalanine,
N$_4$ is any portion of the ghrelin amino acid sequence beginning with the residue at position 5 of SEQ ID NO: 1 and ending at position 28 of SEQ ID NO: 1. Therefore, N$_4$ can be L, LS, LSP, LSPE (SEQ ID NO: 3), LSPEH (SEQ ID NO: 4), LSPEHQ (SEQ ID NO: 5), LSPEHQR (SEQ ID NO: 6), LSPEHQRV (SEQ ID NO: 7), LSPEHQRVQ (SEQ ID NO: 8), LSPEHQRVQQ (SEQ ID NO: 9), LSPEHQRVQQR (SEQ ID NO: 10), LSPEHQRVQQRK (SEQ ID NO: 11), LSPEHQRVQQRKE (SEQ ID NO: 12), LSPE-HQRVQQRKES (SEQ ID NO: 13), LSPEHQRVQQRKESK (SEQ ID NO: 14), LSPEHQRVQQRKESKK (SEQ ID NO: 15), LSPEHQRVQQRKESKKP (SEQ ID NO: 16), LSPE-HQRVQQRKESKKPP (SEQ ID NO: 17), LSPE-HQRVQQRKESKKPPA (SEQ ID NO: 18), LSPE-HQRVQQRKESKKPPAK (SEQ ID NO: 19), LSPEHQRVQQRKESKKPPAKL (SEQ ID NO: 20), LSPE-HQRVQQRKESKKPPAKLQ (SEQ ID NO: 21), LSPE-HQRVQQRKESKKPPAKLQP (SEQ ID NO: 22) or LSPE-HQRVQQRKESKKPPAKLQPR (SEQ ID NO: 23) or conservatively substituted versions thereof. In addition, N$_1$ and N$_4$ may be present or absent. Furthermore, N$_1$, N$_2$, and N$_3$ can be conservatively substituted versions of glycine, serine and phenylalanine, respectively. Other analogs of native ghrelin and its fragments can be found in Bednarek et al., *J Med. Chem.* 2000, 43, 4370-4376. The ghrelin antigens can be used in the methods provided herein.

Figure 15:
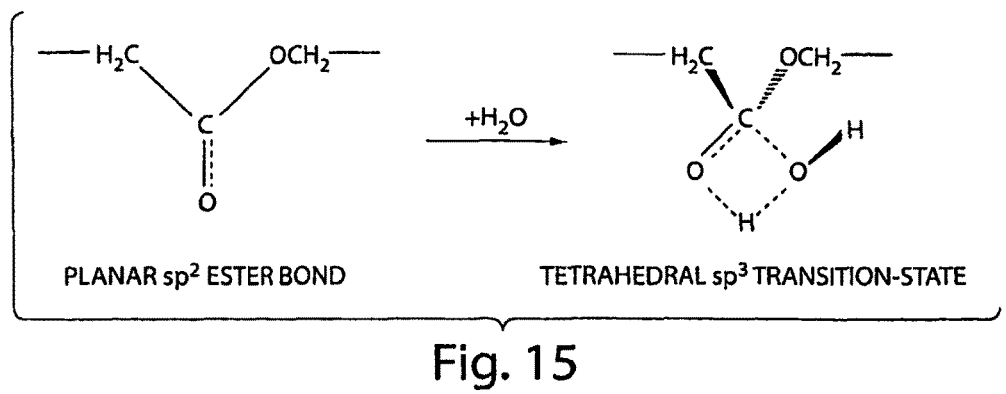
FIG. 15 illustrates the tetrahedral intermediate formed during octyl ester hydrolysis.
Figure 16:
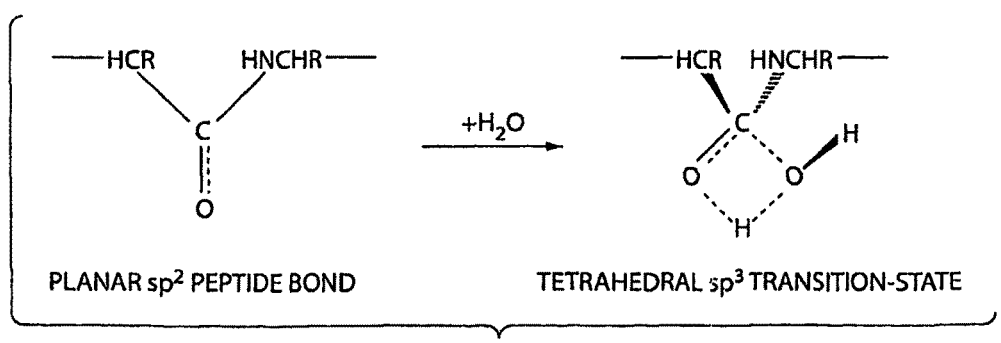
FIG. 16 illustrates the tetrahedral intermediate formed during peptide hydrolysis.

Ghrelin antigens also include ghrelin transition state analogs. As used herein, a "ghrelin transition state analog" is a compound that mimics the transition state (i.e., tetrahedral intermediate) formed during the hydrolysis of the octyl ester from octanoylated native ghrelin (FIG. 15) or the hydrolysis of the peptide of native ghrelin (FIG. 16). Ghrelin transition state analogs, therefore, mimic the tetrahedral intermediate and have a tetrahedral conformation (i.e., sp$^3$) rather than a planar (i.e., sp$^2$) conformation.

Ghrelin transition state analogs include mimics of the tetrahedral intermediate formed during octyl ester hydrolysis. Creating such a ghrelin transition state analog that can generate antibodies that can hydrolyze an ester bond involves changing the physical geometry of the carbonyl carbon at the bond one wants to cleave. That carbonyl carbon is in a characteristic planar sp2 configuration prior to cleavage and, as FIG. 15 shows, this is a flat structure. A water molecule (HOH) adds to this carbonyl carbon to initiate hydrolysis of the ester bond. This creates a transition state that has an sp3 tetrahedron configuration as illustrated in FIG. 15. That transition state is only fleetingly present before the bond between the carbonyl C and adjacent O is severed and hydrolysis is complete. The structure of the ester sp2 bond is planar. In sharp contrast each transition state analog has a tetrahedral sp3 bond which confers a distinctive "kink" at that position. Those bond angle changes are characteristic of the sp3 tetrahedral conformation that makes transition state analogs capable of eliciting catalytic (cleaving) antibodies. This locked-in sp3 tetrahedron geometry allows the generation of catalytic (i.e., cleaving) antibodies. The antibodies elicited predominantly recognize this stereo-chemical alteration not the particular atoms involved in creating the change.

Ghrelin transition state analogs include mimics of the tetrahedral intermediate that occurs during octyl ester hydrolysis. Ghrelin transition state analogs include compositions that comprise a compound of Formula 1.

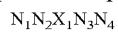

in which
N$_1$ is glycine,
N$_2$ is serine,
X$_1$ is

Figure 17:
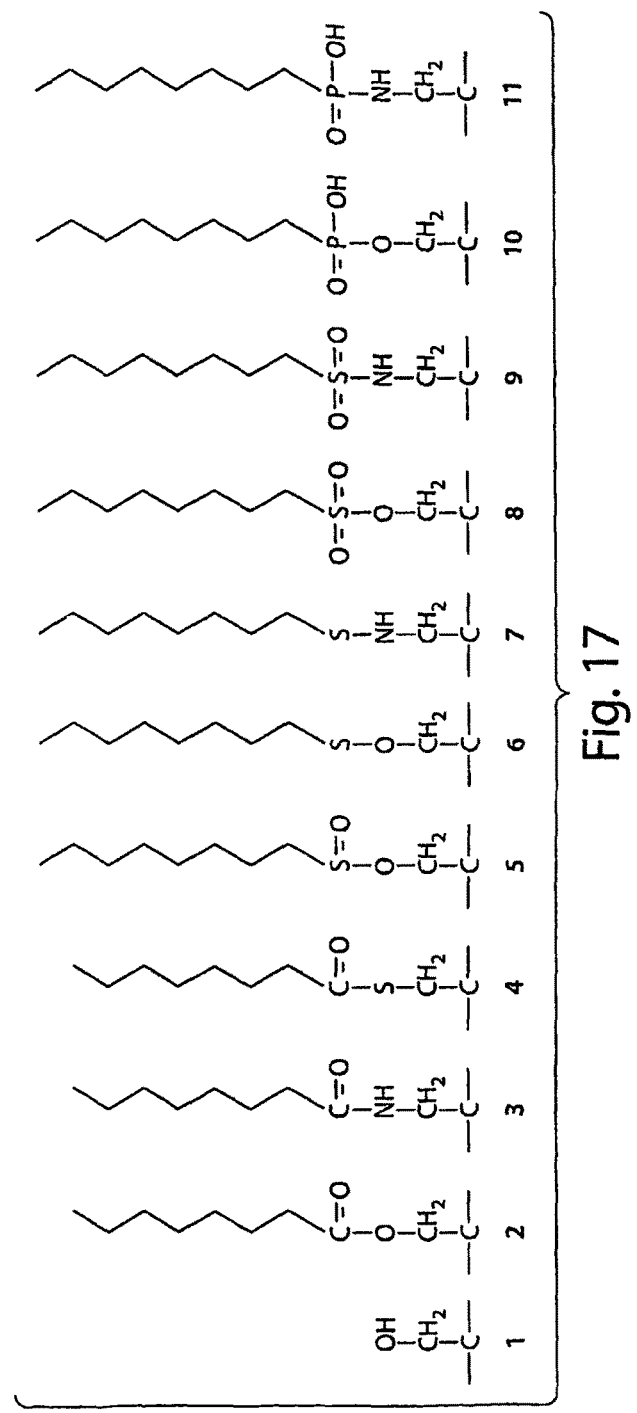
FIG. 17 shows a portion of the active form of native ghrelin that has an octyl ester on the second serine residue (2). The inactive form has no ester at this site (1). Analogs of the octyl ester are shown in molecules 3-11, with 8-11 being transition state analogs of the octyl ester.

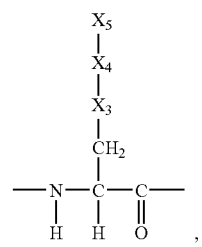

wherein $X_3$ is O or NH, $X_4$ is O=S=O or O=P—OH and $X_5$ is a hydrophobic moiety;

$N_3$ is phenylalanine, and $N_4$ is leucine, and wherein $N_1$ and $N_4$ each may be present or absent. In addition, $N_1$, $N_2$, $N_3$ and $N_4$ can be conservatively substituted versions of glycine, serine, phenylalanine and leucine, respectively. The compound of Formula 1 can, optionally, further include additional consecutive amino acid residues from the native amino acid sequence of native ghrelin (SEQ ID NO: 1) or conservatively substituted versions thereof. In another embodiment $N_4$ of Formula 1 is, alternatively, any portion of the ghrelin amino acid sequence beginning with the residue at position 5 of SEQ ID NO: 1 and ending at position 28 of SEQ ID NO: 1. In another embodiment the ghrelin transition state analog is one that contains at least 3 consecutive amino acids of SEQ ID NO: 1 that include two consecutive serines and a phosphonate or other transition state moiety with tetrahedral geometry on the second serine. In one embodiment the transition state moiety is an analog of the octyl ester, such as those in molecules 8-11 of FIG. 17. In some embodiments the ghrelin transition state analog contains 3, 4, 5, 6, 7, 8, 9, 10, 12, 15, 17, 20, 22, 25 or 28 consecutive amino acids of SEQ ID NO: 1 or a conservatively substituted version thereof. In some embodiments the ghrelin transition state analog is 3, 4, 5, 6, 7, 8, 9, 10, 12, 15, 17, 20, 22, 25, 28, 30, 32, 35, 37, 40, 42, 45, 47 or 50 amino acids in length. In other embodiments the ghrelin transition state analog is at least 3 amino acids in length but less than 50 amino acids in length.

As used herein, a "hydrophobic moiety" is any moiety that is hydrophobic and can be included in a compound as described herein provided that it does not interfere with the desired use of the compound. For instance, in some embodiments hydrophobic moieties include those that do not interfere with the use of the compounds for generating antibodies that bind specifically to and/or cleave octanoylated native ghrelin. In another embodiment, where the hydrophobic moiety is in a ghrelin transition state analog, the hydrophobic moiety is one that does not interfere with the tetrahedral geometry of the ghrelin transition state analog. Preferably, when in a ghrelin transition state analog, the hydrophobic moiety does not interfere with the tetrahedral geometry of the ghrelin transition state analog and does not interfere with the use of the ghrelin transition state analog for generating antibodies that bind specifically to and/or cleave octanoylated native ghrelin. Hydrophobic moieties are well known in the art. Suitable non-limiting examples of hydrophobic moieties include alkyl chains, aliphatic acids, aromatic acids. Alkyl chains and aliphatic acids can include $C_3$, $C_4$, $C_5$, $C_6$, $C_7$, $C_8$, $C_9$, $C_{10}$, $C_{11}$, $C_{12}$, $C_{13}$, $C_{14}$, $C_{16}$, $C_{18}$ or $C_{20}$ chains. Alkyl chains and aliphatic acids can be saturated or unsaturated, branched or unbranched. Hydrophobic moieties in some embodiments also include benzene, 1-adamantaneacetyl groups, etc. Further examples of hydrophobic moieties can be found, for example, in U.S. Pat. Nos. 5,580,899 and 6,995,312. The examples of hydrophobic moieties is incorporated herein by reference.

As used herein, a "conservative amino acid substitution" or "conservative substitution" refers to an amino acid substitution in which the substituted amino acid residue is of similar charge as the replaced residue and is of similar or smaller size than the replaced residue. Conservative substitutions of amino acids include substitutions made amongst amino acids within the following groups: (a) the small non-polar amino acids, A, M, I, L, and V; (b) the small polar amino acids, G, S, T and C; (c) the amido amino acids, Q and N; (d) the aromatic amino acids, F, Y and W; (e) the basic amino acids, K, R and H; and (f) the acidic amino acids, E and D. Substitutions which are charge neutral and which replace a residue with a smaller residue may also be considered "conservative substitutions" even if the residues are in different groups (e.g., replacement of phenylalanine with the smaller isoleucine). Additional examples of conservative substitutions include alanine for glycine; threonine, homoserine and cysteine for serine; tyrosine and tryptophan for phenylalanine; and valine, isoleucine, norleucine and norvaline for leucine. The term "conservative amino acid substitution" also refers to the use of amino acid analogs. Amino acid analogs are well known to those of ordinary skill in the art. Examples of amino acid analogs can be found, for example, in Peptech Corporation's *The Encyclopedia of Amino Acid Analogs and Chiral Building Blocks* 2003-2004, peptechcorp.com/documents/PepTech2003_2004.pdf.

Ghrelin transition state analogs also include mimics of the tetrahedral intermediate formed during peptide hydrolysis. As described above, the starting point required to generate antibodies that can hydrolyze a peptide bond involves changing the physical geometry of the carbonyl carbon at the bond one wants to cleave. That carbonyl carbon is in a characteristic planar (sp2) configuration prior to cleavage and is a flat structure. A water molecule (HOH) adds to this carbonyl carbon to initiate hydrolysis of the peptide bond. This creates a transition state that has an sp3 tetrahedron configuration as illustrated in FIG. 16. That transition state is also only fleetingly present before the bond between the carbonyl C and adjacent N is severed and hydrolysis is complete. Again, the sp3 tetrahedron geometry allows for the generation of antibodies that predominantly recognize this stereo-chemical alteration not the particular atoms involved in creating that change.

Therefore, ghrelin transition state analogs include ghrelin peptides that contain at least 3 or more consecutive amino acids of SEQ ID NO: 1 or conservatively substituted versions thereof, wherein at least one of the peptide bonds (i.e., —CO—NH—) has been replaced with a statyl moiety (i.e., —CHOH—CH$_2$—CO—NH—) or a reduced peptide bond (i.e., —CH$_2$—NH$_2$$^+$—). The peptide bond that is replaced can be any of the peptide bonds between the amino acids or conservatively substituted versions of a ghrelin peptide. In some embodiments the peptide bond that is replaced is at or near the N-terminal portion of a ghrelin peptide. "At or near the N-terminal portion" refers to a bond at the N-terminus of a peptide or a bond between two residues that are within the first half of the peptide. In other embodiments where the bond that is replaced is between residues 1 and 2, 2 and 3, 3 and 4, 4 and 5, 5 and 6, 6 and 7, etc. Preferably, the reduced peptide bond elicits a complementary negatively charged side chain at a proximal locus in the antibody combining site. Such a ghrelin transition state analog can optionally include an octyl ester or analog thereof. The ghrelin transition state analog can contain in some embodiments 3, 4, 5, 6, 7, 8, 9, 10, 12, 15, 17, 20, 22, 25 or 28 consecutive amino acids of SEQ ID NO: 1 or a conservatively substituted version thereof. In other embodiments the ghrelin transition state analog is 3, 4, 5, 6, 7, 8, 9, 10, 12, 15, 17, 20, 22, 25, 28, 30, 32, 35, 37, 40, 42, 45, 47 or 50 amino acids in length. In a further embodiment the ghrelin transition state analog is at least 3 but less than 50 amino acids in length. The statyl moiety can be derived from a protease transition state inhibitor, such as amastatin, pepstatin and bestatin. Methods of producing transition state analogs are known to those of ordinary skill in the art. In addition, techniques for producing such transition state analogs are provided in U.S. Pat. No. 6,872,554, the contents of such techniques are incorporated herein by reference. In one embodiment the ghrelin transition state analog contains at least three consecutive amino acids from the N-terminal portion of the native ghrelin sequence with at least one of the peptide bonds therein being replaced with a statyl moiety or a reduced peptide bond. Preferably, such a ghrelin transition state analog can generate antibodies that cleave octanoylated native ghrelin.

In some embodiments the ghrelin antigen can further comprise a linker, such as a cysteine, added to the carboxyl terminus. The added linker is used in some embodiments to link a ghrelin antigen to a carrier molecule (e.g., a carrier protein, such as maleimide-activated carrier protein or Keyhole Limpet Hemocyanin (KLH)). The linker can also be used to link a ghrelin antigen to a detectable moiety. Additional linkers are well known in the art and include 4-[p-azidosalicylamido] butylamine and 1-ethyl-3-[[3-dimethylaminopropyl]-carbodiimide hydrochloride. When a ghrelin antigen, such as a ghrelin transition state analog, is one that contains fewer than 7 or 8 amino acids, it may be preferable that the ghrelin antigen is conjugated to a linker.

Antibodies can also be produced with any of the ghrelin antigens provided. Once produced, the antibodies that specifically bind and/or cleave octanoylated native ghrelin can be selected. Methods for selecting such antibodies are known in the art, and examples of which, are provided below in the Examples. It has been discovered that catalytic antibodies, antibodies that cleave octanoylated native ghrelin, can be produced. Some catalytic antibodies can continuously inactivate circulating ghrelin by hydrolytically cleaving its octyl ester. Some catalytic antibodies cleave the peptide backbone of octanoylated native ghrelin. Preferably, cleavage of the peptide backbone occurs in the N-terminal portion of ghrelin. Catalytic antibodies provide a highly efficient and permanent means of depleting ghrelin in the blood. The stereochemical modification of the transition state analogs can mimic the ester bond during its hydrolysis. An antibody with a binding site complementary to a tetrahedral transition state analog can force the normally planar bond of the octanoyl ester into a transition state-like conformation (i.e., a tetrahedral conformation). Such bond distortion plus the participation of antibody acid/base side chain groups can catalyze the hydrolytic cleavage and render the peptide inactive. As provided above transition state analogs include the compounds of Formula 1 as well as ghrelin peptides engineered to contain a statyl moiety or reduced peptide bond. In one embodiment the ghrelin transition state analogs are not themselves hydrolyzable.

The antibodies provided herein also include modified versions of the antibodies. Modified antibodies include antibody conjugates or genetic constructs thereof, where the antibodies are conjugated to other biomolecules (e.g., polyethylene glycol (PEG), albumin or albumin-binding peptide) that would, for example, prolong the serum half-life of an anti-ghrelin antibody (e.g., a scFv antibody). In other words, these biomolecules can prolong the residence time of an agent in the body. A "biomolecule that prolongs the residence time of an agent in the body" is one which results in the presence of the agent in the body of a subject for a longer period of time or in a higher amount at a particular point in time than when the agent is administered without the biomolecule. An appended Cys residue can be used as a point of attachment for creating such antibody conjugates. Techniques for making such conjugates are known to those of ordinary skill in the art and are described herein in the Examples as well as in Smith et al., *Bioconjugate Chem.* 2001, 12, 750-756.

Any given anti-ghrelin antibody can also be modified by genetic engineering to achieve higher affinity (e.g., higher affinity to octanoylated native ghrelin), bivalent binding or facilitated passage into the CNS (Pardridge, W. M., et al. 1991. *J Pharmacol Exp Ther* 259:66-70.) For instance, mutagenic PCR can be used to evolve anti-ghrelin antibodies, such as scFv antibodies, toward higher binding affinities and greater functionality. Briefly, for molecular evolution, an anti-ghrelin scFv DNA is amplified using error-prone PCR to incorporate 3 to 7 point mutations/scFv. The material is then cloned into a surface expression vector using the endogenous homologous recombination system present in yeast. This allows mutated libraries of $1-10 \times 10^6$ clones to be rapidly generated and screened. Mutagenic PCR can also be used to generate catalytic antibodies with an increased turnover number ($k_{cat}$) for cleaving the octanoyl group from ghrelin. Preferably, modified anti-ghrelin antibodies that are engineered to allow their passage into the CNS include scFv antibodies, diabodies or other anti-ghrelin antibody fragments. Any of the isolated anti-ghrelin scFv antibodies can be evolved into a higher affinity version to increase its therapeutic effectiveness (Boder, E. T., et al. 2000. *Proc Natl Acad Sci USA* 97:10701-10705.)

The antibodies of the present invention can, therefore, be in the form of a bispecific antibody, or a multispecific antibody. The term "bispecific antibody" is intended to include any agent, e.g., a protein, peptide, or protein or peptide complex, which has two different binding specificities. The term "multispecific antibody" is intended to include any agent, e.g., a protein, peptide, or protein or peptide complex, which has more than two different binding specificities. The term "bispecific antibodies" further includes diabodies. Diabodies are bivalent, bispecific antibodies in which the $V_H$ and $V_L$ domains are expressed on a single polypeptide chain, but using a linker that is too short to allow for pairing between the two domains on the same chain, thereby forcing the domains to pair with complementary domains of another chain and creating two antigen-binding sites (see e.g., Holliger, P., et al. (1993) *Proc. Natl. Acad. Sci. USA* 90:6444-6448; Poijak, R. J., et al. (1994) *Structure* 2:1121-1123).

The antibodies can be structurally modified to achieve bivalent binding. There are several different approaches that can be taken to create homo- or hetero-dimers. For instance, a carboxyl-terminal Gly$_4$Cys linker moiety can be added to a scFv antibody (Huston, J., et al. 1994. *Cell Biophys.* 24-25: 267-278; Adams G., 1993. *Cancer Res.* 53: 4026-4034). The Cys thiol is stabilized and Ellman's reagent (E) is used to activate this group on one of the scFv components, so that it will react unidirectionally with the second via disulfide exchange. Alternatively, a Cys linker can also be used for conjugation. Antibodies as provided herein also include antibodies with a detectable moiety, such as biotin or a fluorescent label.

One way of delivering antibodies to the brain is by producing vectorized antibodies competent for transcytosis across the blood-brain barrier. Vectorized antibodies are produced by covalently linking an antibody to an agent which promotes delivery from the circulation to a predetermined destination in the body. Examples of vectorized molecules which can traverse the blood-brain barrier are found in Bickel et al., Proc. Natl. Acad. Sci. USA 90: 2618-2622 (1993) and Broadwell et al., Exp. Neurol. 142: 47-65 (1996). In these examples, antibodies are linked to another molecule, the antibodies being the agent which promotes delivery of the molecule. One example of such an agent is an antibody which is directed towards a cell surface component, such as a receptor, which is transported away from the cell surface. Examples of antibodies which confer the ability to trancytose the blood-brain barrier include, without limitation, anti-insulin receptor antibodies, and also anti-transferrin receptor antibodies (Saito et al., Proc. Natl. Acad. Sci. USA 92: 10227-31 (1995); Pardridge et al., Pharm. Res. 12: 807-816 (1995); Broadwell at al., Exp. Neurol. 142: 47-65 (1996)). The antibodies or antigen-binding fragments thereof provided herein, therefore, can be conjugated to ligands, such as antibodies, which bind receptors on the blood-brain barrier (e.g., insulin, transferrin, or low density lipoprotein).

Agents that inactivate octanoylated native ghrelin also include enzymes that cleave octanoylated native ghrelin. Such enzymes include enzymes that cleave the octyl ester or the peptide backbone of octanoylated native ghrelin. The enzymes can be, for example, an esterase, such as a butyryl cholinesterase or carboxylesterase. The enzymes can also be, for example, dipeptidyl peptidase I, II, III or IV, neprylsin, aminopeptidase N, cytosol alanyl aminopeptidase or cathepsin H. In some embodiment the enzyme is a rat or porcine form of the enzyme. In another embodiment the enzyme is the human form of the enzyme. In still another embodiment the enzyme is human serum butyryl cholinesterase or human carboxylesterase.

Agents that inactivate octanoylated native ghrelin also include agents that generate anti-ghrelin antibodies when administered to a subject. Preferably, these agents cause anti-ghrelin antibodies that inactivate octanoylated native ghrelin to be produced. Active vaccines, as used herein, refer to compositions comprising such agents. These agents include ghrelin antigens, such as the compounds of Formula 1 and Formula 2, modified versions and conjugates thereof.

In one aspect of the invention the active vaccines provided can be used in a method of generating anti-ghrelin antibodies. Such methods include administering an agent as described above to a subject in an amount effective to generate anti-ghrelin antibodies. In one embodiment the method further includes the administration of an adjuvant to the subject. The adjuvant can be administered prior to, concomitantly with or subsequent to the administration of the compound. Adjuvants, as provided herein, include complete Freunds and incomplete Freunds adjuvant. Other adjuvants are well known to those of ordinary skill in the art. The method can further comprise administering one or more booster doses of a ghrelin antigen, which can be the same or different from the agent previously administered. As used here, an "effective amount to generate anti-ghrelin antibodies" refers to the amount of the compound alone or in combination with an adjuvant or other ghrelin antigen that can be used to generate anti-ghrelin antibodies in the subject. In one embodiment the effective amount is also effective in inactivating octanoylated native ghrelin. In another embodiment the inactivation is by the specific binding and/or cleavage of octanoylated native ghrelin. In another embodiment the effective amount is an amount effective to suppress appetite stimulation and/or to treat obesity. In yet another embodiment the effective amount is an amount effective to treat PWS. "An effective amount for suppressing appetite stimulation" is any amount of the compound alone or in combination that slows or eliminates appetite. "An effective amount for treating obesity" is an amount of the compound alone or in combination that slows or reverses weight gain in a subject. "An effective amount for treating PWS" is any amount of the compound alone or in combination that alleviates or eliminates any symptom of PWS (e.g., uncontrolled appetite, hyperphagia and/or obesity).

The active vaccine can also be in the form of a DNA vaccine whereby the DNA vaccine encodes a ghrelin antigen (i.e., ghrelin polypeptide) and is administered to a subject. Vectors suitable for use in this context are well known to those of ordinary skill in the art. For example, plasmid vectors and viral vectors have been used as DNA vaccines for delivering antigen-encoding nucleic acids to cells in vivo. Plasmid vectors are particularly advantageous because they do not have the same safety concerns as with some of the viral vectors. These plasmids, however, having a promoter compatible with the host cell, can express a peptide from a nucleic acid operatively encoded within the plasmid. Some commonly used plasmids include pBR322, pUC18, pUC19, pRC/CMV, SV40, and pBlueScript. Additionally, plasmids may be custom designed using restriction enzymes and ligation reactions to remove and add specific fragments of DNA. Plasmids such as those used for DNA vaccines may be delivered by a variety of parenteral, mucosal and topical routes. For example the plasmid DNA can be injected by intramuscular, intradermal, subcutaneous or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation. Further, DNA vaccines can be administered to a subject in conjunction with an adjuvant or additional therapeutic agent. The administration of an adjuvant or additional therapeutic agent can occur prior to, concomitantly with or subsequent to the administration of the DNA vaccine.

In some embodiments the methods of administration of a ghrelin antigen or DNA vaccine further include determining whether or not anti-ghrelin antibodies that specifically bind and/or cleave octanoylated native ghrelin are produced. Such a determination can include the harvesting of a sample that contains antibodies from the subject and assessing whether the sample includes one or more antibodies that specifically bind and/or cleave octanoylated native ghrelin. Binding of peptides to antibodies can be determined using standard methodologies including surface plasmon resonance and ELISA assays. This as well as other methods for such assessment are well known to those of ordinary skill in the art and further examples of which are provided below in the Examples. The methods provided can further involve the steps of selecting compositions for administration that can generate the desired antibodies. In one embodiment antibodies that specifically bind octanoylated native ghrelin are desired. In another embodiment antibodies that cleave octanoylated native ghrelin are desired. In yet another embodiment antibodies that bind or cleave as well as inactivate an activity of native ghrelin are desired.

As used herein, to "inactivate native ghrelin" or "inactivate an activity of native ghrelin" refers to the elimination or reduction of an activity of native ghrelin, and an "amount effective to do so" is the amount of an agent alone or in combination (with an adjuvant or additional therapeutic agent) that results in the elimination or reduction of native ghrelin activity. Preferably, its activity is its hunger response activity. Therefore, the agents provided can be used to inhibit or reduce appetite stimulation in a subject. Additionally, the agents provided can also be used in the treatment of obesity in a subject.

As used herein, the "treatment of obesity in a subject" refers to the slowing or reversal of weight gain in a subject. In one embodiment the subject is considered obese (body mass index >30) or morbidly obese (body mass index >40). Treatment of obesity in a subject also encompasses the slowing or reversal of weight gain in a subject, so that becoming obese is prevented. Treatment of obesity in a subject also, therefore, refers to the prevention of obesity in the subject.

As used herein, a "subject" includes any individual who would benefit from the inactivation of native ghrelin. These subjects as described above include those individuals who are obese or are at risk of becoming obese. The subjects also include those with higher than normal levels of ghrelin. In addition, the subjects as provided herein include individuals who have or are at risk for developing hypertension, type 2 diabetes, heart disease, stroke, cancer or any other condition or disorder in which being obese or having a higher level of ghrelin than normal or that is needed is a causative or an associated factor. Such conditions or disorders are also referred to herein as "conditions or disorders associated with or caused by ghrelin". The compositions of the agents provided herein can be administered to any such subjects. In addition, methods of their treatment through the administration of the compositions and agents as described herein are also provided.

The agents provided herein, therefore, can also be used to treat PWS patients in order to prevent or treat their uncontrolled appetite, hyperphagia and/or obesity. PWS is a chromosomal disorder marked by extreme obesity, mental retardation, and other problems. It afflicts approximately 1 in 15,000 children worldwide. Children with Prader-Willi syndrome have unusually high levels of ghrelin (Haqq, A. M., et al. 2003. *J Clin Endocrinol Metab* 88:174-178.) PWS occurs in all ethnicities and to the same extent in males and females. Ghrelin has been found to be elevated 3- to 5-fold in PWS patients versus non-PWS subjects. While PWS is a multi-symptomatic disease, obesity is a common attribute of the condition and contributes substantially to its morbidity. Mortality in PWS is due to ancillary health conditions which stem directly from obesity and can include hypertension, diabetes, respiratory problems, heart failure, stroke or additional medical problems. Also included as subjects, therefore, are those who suffer from PWS.

The compositions and methods provided can further include other therapeutic agents or treatment regimens for suppressing appetite or treating obesity. Other treatment regimens include radical gastric bypass surgery. Interestingly, a study of gastric bypass patients indicates that the mechanisms underlying the dramatic effects of such surgery may go beyond the physical small size of the residual gastric pouch (Cummings, D. E., D. S. Weigle, R. S. Frayo, P. A. Breen, M. K. Ma, E. P. Dellinger, and J. Q. Purnell. 2002. N Engl J Med 346: 1623-). The major effect is likely due to a markedly reduced production or secretion of ghrelin by the modified stomach. The study shows that normal weight people and matched obese controls (no surgery) had plasma ghrelin levels that ranged between 100-200 pM, and gastric bypass patients had levels of only 40 pM throughout the 24-hour monitoring period. Moreover, ghrelin levels spiked just before breakfast, lunch and dinner for the normal and matched obese subjects but were amazingly flat over the entire 24-hour time course for the bypass patients. It has been estimated that about 150,000 gastric bypass surgeries will be performed this year in the U.S. This procedure can result in the loss of hundreds of pounds and effects are known to persist for 14 years or more (Mun, E. C., et al. 2001. *Gastroenterology* 120:669-681.) Other therapeutic agents that can be combined with the agents provided herein include any recognized therapeutic agent for appetite suppression or weight control. Such therapeutic agents include 5-HT modulating drugs; beta 3 adrenoreceptor agonists; lipase inhibitors; melanocortin 4 agonists; and leptin agonists. Leptin agonists have created interest since they are able to reduce feeding. Recent studies, however, have shown that obese individuals produce high levels of leptin and eventually become resistant to leptin. Other additional therapeutic agents include sibutramine (Reductil/Meridia), Xenical (orlistat) and Obistatin. Sibutramine works to suppress the appetite primarily by inhibiting the reuptake of the neurotransmitters norepinephrine and serotonin. Orlistat is a lipase inhibitor. Obistatin is part the same prohormone gene that gives rise to ghrelin but has an opposing action in weight regulation. The use of anti-ghrelin antibodies, ghrelin inactivating enzymes or active vaccines as provided herein in combination with these or other additional therapeutic agents can, in some instances, produce a greater therapeutic effect than a single therapeutic agent alone.

The invention provides compositions comprising the agents provided herein. The compositions can include a physiologically or pharmaceutically acceptable carrier, excipient, or stabilizer mixed with the agent. Pharmaceutical compositions of the invention also can be administered in combination therapy, i.e., combined with other agents. For example, the combination therapy can include a composition of the present invention with at least one other agent for suppressing appetite, controlling weight gain or treating obesity.

As used herein, "pharmaceutically acceptable carrier" or "physiologically acceptable carrier" includes any and all salts, solvents, dispersion media, coatings, antibacterial and antifungal agents, isotonic and absorption delaying agents, and the like that are physiologically compatible. In some embodiments, the carrier is suitable for intravenous, intramuscular, intraperitoneal, subcutaneous, parenteral, spinal or epidermal administration (e.g., by injection or infusion). Depending on the route of administration, the agent may be coated in a material to protect the agent from the action of acids and other natural conditions that may inactivate the agent.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents, such as supplementary immune potentiating agents including adjuvants, chemokines and cytokines. When used in medicine, the salts should be pharmaceutically acceptable, but non-pharmaceutically acceptable salts may conveniently be used to prepare pharmaceutically-acceptable salts thereof and are not excluded from the scope of the invention.

A salt retains the desired biological activity of the parent compound and does not impart any undesired toxicological effects (see e.g., Berge, S. M., et al. (1977) *J. Pharm. Sci.* 66: 1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

The compositions provided can be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the agents of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well-known in the art of pharmacy. All methods include the step of bringing an agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for parenteral administration conveniently comprise a sterile aqueous or non-aqueous preparation of an agents as provided herein, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulations suitable for oral, subcutaneous, intravenous, intramuscular, etc. administration can be found in *Remington's Pharmaceutical Sciences*, Mack Publishing Co., Easton, Pa.

The agents can be prepared with carriers that will protect them against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

The therapeutics of the invention can be administered by any conventional route, including injection or by gradual infusion over time. The administration may be, for example, mucosal (e.g., oral, buccal, nasal), intravenous, intraperitoneal, intramuscular, intracavity, subcutaneous, parenteral or intradermal. The administration can also be by nasal administration. In some embodiments where a vaccine is administered, the administration is preferably intradermal, subcutaneous, intraperitoneal or intramuscular. When antibodies are used therapeutically, preferred routes of administration include intravenous, intraperitoneal, intracranial, mucosal (e.g., oral, buccal, nasal), parenteral, intrapulmonary, by suppository or by local or targeted delivery. The antibodies in some embodiments can be administered intracerebrally by periodic bolus injection or by sustained infusion using a pump. In one embodiment where an antibody composition is administered the administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in *Remington's Pharmaceutical Sciences*, 18th edition, 1990, pp. 1694-1712; incorporated by reference). Those of skill in the art can readily determine the various parameters and conditions for producing aerosols without resorting to undue experimentation. In some embodiments where passage of the agents through the blood brain barrier is desired, the agents or compositions provided can be administered intravenously. In other embodiments where administration to the vagus nerve is desired the agents or compositions provided are administered intraperitoneally. In another embodiment the administration is such that an effective amount of a therapeutic composition as provided herein is administered to or reaches the stomach.

The immunological approach of using either active or passive vaccines offers distinct advantages for reducing ghrelin levels in the body. For example, active immunization can elicit anti-ghrelin antibodies that will be present to act therapeutically 24 hours a day, 7 days a week for years with periodic boosting. Thus long-term weight maintenance can be attainable.

The compositions of the invention are administered in effective amounts. An "effective amount" is that amount of a composition as provided herein that alone, or together with further doses, adjuvants or additional therapeutic agents, produces the desired response, e.g., reduces or eliminates native ghrelin activity, suppresses appetite, treats obesity in a subject or treats a subject with PWS. This may involve only slowing the weight gain temporarily, although more preferably, it involves long term weight control. The desired response to treatment of the disease or condition also can be delaying the onset or even preventing weight gain. The effects of treatment can be monitored by routine methods. Such methods can be indirect or direct methods. For instance, the effects can be monitored by radioimmunoassay of antibody levels in a subject or by assessing the levels of free ghrelin in the subject's blood. The effects can also be measured by determining the extent of the weight loss or the reduction in weight gain by determining the change in weight in a subject. The effects can also be measured by determining the extent of a reduction or elimination of a symptom associated with a condition or disorder caused by or associated with ghrelin. Other assays will be known to one of ordinary skill in the art and can be employed for measuring the level of the response to treatment.

Such amounts will depend, of course, on the severity of the obesity or the risk thereof, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. Concentrations of antibody that are sustainable in animals can far exceed the levels of circulating ghrelin. For example, in both normal and obese people the plasma concentration of ghrelin ranges from 100-200 pM while gastric bypass patients have hormone levels of about 40 pM. The medium-range plasma level of a specific antibody in an immunized animal is 1,000,000 pM (~150 µg/ml). It will be understood by those of ordinary skill in the art, however, that a patient may insist upon a lower dose or tolerable dose for medical reasons, psychological reasons or for virtually any other reason.

The pharmaceutical compositions used in the foregoing methods preferably are sterile and contain an effective amount of an agent for producing the desired response in a unit of weight or volume suitable for administration to a patient.

The doses administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

In general, when a vaccine, such a ghrelin antigen composition, is administered doses range from about 10 micrograms to 1 milligram. In some embodiments the dose of a vaccine is between 10 micrograms to 100 micrograms, 100 micrograms to 500 micrograms, or 500 micrograms to 1 milligram. In general, when an antibody composition is administered the dose is between 0.5 milligrams to 100 milligrams. In one embodiment, the dose is about 1 mg. In another embodiment the dose is about 10 mg. In yet a further embodiment the dose is about 25 mg. In a further embodiment the dose is about 50 mg. In another embodiment, the dose is about 100 mg.

Based upon the composition, the dose can be delivered once, continuously, such as by continuous pump, or at periodic intervals. The periodic interval may be weekly, bi-weekly or monthly. The dosing can occur over the period of one month, two months, three months or more to elicit an appropriate humoral and/or cellular immune response. Desired time intervals of multiple doses of a particular composition can be determined without undue experimentation by one skilled in the art.

In the event that the response in a subject is insufficient at such doses, higher doses (or effective higher doses by a different, more localized delivery route) may be employed to the extent that patient tolerance permits. Other protocols for the administration of the compositions provided will be known to one of ordinary skill in the art, in which the dose amount, schedule of administration, sites of administration, mode of administration and the like vary from the foregoing.

The compositions of the present invention have in vitro and in vivo utilities. For example, these molecules can be administered to a sample, e.g. in vitro or ex vivo, or in a subject, e.g., in vivo, to treat obesity or reduce or eliminate native ghrelin activity.

As another example the antibodies or ghrelin antigens provided can be used in various screening methods. In one embodiment the screening method includes the step of contacting a candidate agent (e.g., one or more antibodies or enzymes that are thought to possibly be able to specifically bind and/or cleave octanoylated native ghrelin and/or inactivate it) with a composition comprising a ghrelin antigen (e.g., octanoylated native ghrelin, active fragment thereof or a ghrelin transition state analog) and determining whether or not the candidate agent binds, cleaves and/or inactivates the ghrelin antigen. As used herein a "candidate ghrelin inactivating agent" is any agent that could be screened in the method provided for its ability to inactivate an activity of native ghrelin (e.g., its hunger response activity). In one embodiment the ghrelin antigen comprises a compound of Formula 1 or Formula 2. In another embodiment the ghrelin antigen is labeled. The label can be any detectable label, such as, for example, biotin or a fluorescent molecule. The label can also be a radioactive label.

As used herein, the term "subject" is intended to include humans and non-human animals, such as mice and non-human primates. Administration of the compositions to mammals other than humans, e.g. for testing purposes or veterinary therapeutic purposes, can be carried out under conditions as described herein.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1

Ghrelin-Specific Antibodies Production, Isolation and Characterization

Synthesis of Ghrelin Peptide Antigens

The amino acid sequence of the 28 residue human ghrelin peptide is shown in FIG. 2. Two octanoylated peptide antigens were designed to elicit an immune response directed against human ghrelin. The first was comprised of the N-terminal 5 amino acids ($G_{1-5}$), while the second encompassed the full-length 28 amino acid human ghrelin sequence ($G_{1-28}$). A cysteine (Cys) residue was added at the C-terminus and each peptide was synthesized using standard automated Fmoc chemistry. The n-octanoyl group was coupled to the second serine by following a published method (Bednarek, M. A., et al. 2000. *J Med Chem* 43:4370-4376.) These ghrelin peptides were purified using HPLC, and their composition was verified by mass spectral and amino acid analysis. The Cys addition was designed to provide a sulfhydryl linkage group for coupling the peptides to maleimide-activated carrier proteins, such as Keyhole Limpet Hemocyanin (KLH).

To synthesize a transition state analog antigen with the potential for eliciting catalytic antibodies, the first 5 amino acids of ghrelin as a backbone was used. Instead of adding 1-octanoic acid to the second serine, 1-octylphosphonic acid was used to create a ghrelin octyl phosphonate rather than the naturally occurring carboxylic ester. A C-terminal Cys residue was added to allow coupling to maleimide-activated carrier proteins. This ghrelin transition state analog peptide ($G_{1-5}$P) was purified using HPLC, and its composition was verified by mass spectral analysis.

Figure 3:
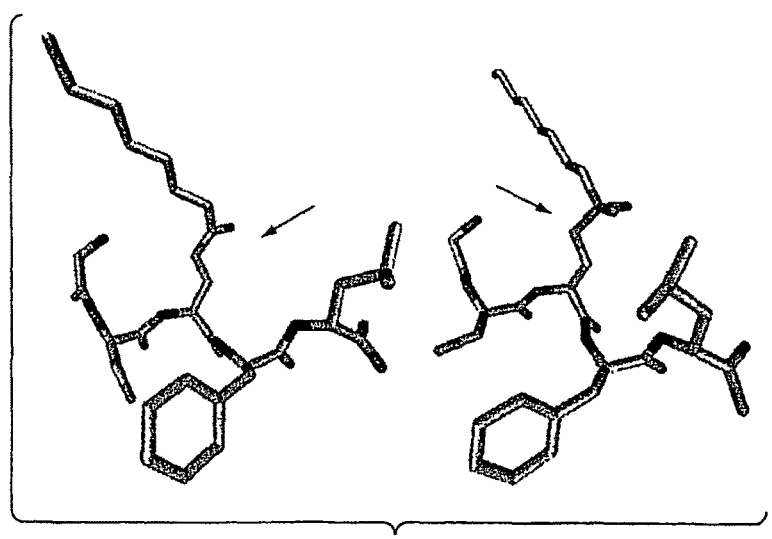
FIG. 3 provides a 3-D model of $G_{1-5}$ (left) and $G_{1-5}P$ (a ghrelin transition state analog) (right).

FIG. 3 provides a 3-D structural comparison of the $G_{1-5}$ carboxylic ester (left) and $G_{1-5}$P transition state analog (right). Both primary amino acid sequences are G S S F L (SEQ ID NO: 24), but the two different octanoyl substituents added to the second serine are conformationally distinct. The naturally occurring ester configuration is $sp^2$ planar while the phosphonate is $sp^3$ tetrahedral (arrows). This $sp^3$ geometry mimics the transition state during hydrolytic cleavage of the ester and can elicit catalytic antibodies.

Production of Anti-Ghrelin Antibodies in Mice and Monkeys

The three different antigens constructed by linking either $G_{1-5}$, full-length ghrelin or the ghrelin phosphonate transition state analog to KLH were used to immunize BALB/c mice. Briefly, this procedure used i.p. injection of the different antigens emulsified in complete Freunds adjuvant, followed by a second course in incomplete Freunds adjuvant. Three days prior to the hybridoma fusion, the BALB/c mice were boosted i.v. with antigen in PBS.

Groups of mice that had been immunized with the three different ghrelin-KLH antigens ($G_{1-5}$, $G_{1-28}$ and $G_{1-5}P$) were bled and tested by ELISA for the presence of ghrelin-specific antibodies. Spleen cells from immunized mice with the highest titer sera were fused with mouse myeloma NS-1 or P3 cells (American Type Culture Collection, Manassas, Va.) to establish hybridomas according to standard procedures. After performing several different fusions, hybridoma clones that produced monoclonal antibodies, which selectively interacted with $G_{1-5}$, $G_{1-28}$ as well as the $G_{1-5}P$ transition state analog, were obtained.

Selected hybridoma cells that made antibodies against the three different ghrelin peptides were injected into separate pristane-primed mice. This gave rise to ascites fluid containing high levels of each of the distinct types of anti-ghrelin antibodies. Alternatively, hybridoma cells can be cultured for antibody production. Those antibodies were purified on protein A affinity columns and characterized by ELISA assays using different ghrelin peptides. Additional ion exchange and molecular sizing steps can be used to further purify the anti-ghrelin antibodies. Antibody Fab fragments can also be generated and purified.

In contemplation of anti-ghrelin vaccine therapy for obesity in people, the ghrelin peptides were tested for safety in non-human primates. Three separate Cynomolgus monkeys (*Macaca fascicularis*) were vaccinated monthly, i.m., with 100 µg of either KLH-linked $G_{1-5}$, full-length ghrelin or the ghrelin phosphonate transition state analog emulsified with incomplete Freunds adjuvant. The animals were bled periodically so that anti-ghrelin antibody levels could be monitored in their serum (diluted 1/100 or 1/500) by ELISA. Table 1 shows the progressive immune response of the monkeys inoculated with $G_{1-5}$-KLH and the specificity of binding to the three ghrelin peptides.

TABLE 1

Serum Antibodies Present in G1-5 Vaccinated Monkeys ELISA Reading (O.D. 450 nm)

| Ghrelin Peptide on Plate | Pre-Vaccination | Primary | 1st boost | 2nd boost |
|---|---|---|---|---|
| G1-5 | 0.078 | 0.965 | 2.361 | 2.754 |
| G1-5P | 0.439 | 0.633 | 0.637 | 0.715 |
| G1-28 | 0.209 | 0.771 | 1.870 | 1.758 |

Table 2 similarly shows the progressive immune response of the monkeys inoculated with $G_{1-28}$-KLH and the specificity of binding to the three ghrelin peptides. The three monkeys each produced antibodies which preferentially bound to the immunogen but cross-reacted to different degrees with the other related ghrelin peptides.

TABLE 2

Serum Antibodies Present in G1-28 Vaccinated Monkeys ELISA Reading (O.D. 450 nm)

| Ghrelin Peptide on Plate | Pre-Vaccination | Primary | 1st boost | 2nd boost |
|---|---|---|---|---|
| G1-5 | 0.104 | 0.158 | 0.111 | 0.067 |
| G1-5P | 0.086 | 0.086 | 0.000 | 0.135 |
| G1-28 | 0.209 | 0.310 | 1.353 | 1.712 |

All of the vaccinated monkeys remained healthy after a primary and several booster injections. They all produced antibodies against ghrelin and KLH. These highly sensitive primates appeared compatible with the anti-ghrelin antibodies that were produced in their bodies for approximately 2 years. Apparently, there are no side effects due to reactions of the endogenous anti-ghrelin antibodies with the hormone, with its precursor protein or with other vital components. No signs of eating/weight disorders, autoimmune disease, immune complex disease or any other adverse/toxic reaction to vaccination have been observed.

Cynomolgus monkeys (*Macaca fascicularis*) can also be passively immunized weekly, iv., with 10 mg of a chosen anti-ghrelin antibody (e.g., a single chain Fv (scFv) antibody) and observed for any ill effects. Periodically, the animals can be bled and a spinal tap taken to monitor human anti-ghrelin antibody levels in their serum and cerebrospinal fluid. After two years, the animals can be autopsied by a pathologist to detect any pertinent immunological or neurological consequences. Effectiveness of these agents to reduce biologically active ghrelin levels in the blood can be monitored with radioimmunoassays.

Ghrelin-Specific Single Chain Fv Antibodies Screening

Biotinylated ghrelin peptides were synthesized to screen a yeast recombinatorial surface display library for different ghrelin-specific human scFv antibodies. A modified automated Fmoc chemistry was used to synthesize ghrelin-PEG-biotin peptides (a $G_{1-5}$ biotin peptide ($G_{1-5}$biotin), a full-length ghrelin biotin ($G_{1-28}$biotin) peptide and a biotinylated ghrelin transition state analog peptide ($G_{1-5}$Pbiotin)), and the n-octanoyl group, or 1-octylphosphonic acid in the case of $G_{1-5}$Pbiotin, was coupled to the second serine by a previously published method (Bednarek, M. A., et al. 2000. *J Med Chem* 43:4370-4376.) A commercially available biotin resin (N-biotinyl-N'-Fmoc-PEG-diamine-MPB-AM resin (Nova Biochem, San Diego, Calif.)) was used, as it placed the biotin group and PEG spacer at the C-terminal end of the ghrelin peptides and allowed for the simultaneous interaction of these probes with both a scFv and streptavidin detector molecule with little to no steric hindrance. The peptides were purified by HPLC and characterized by mass spectral analysis.

The biotinylated ghrelin peptides were used to screen a yeast recombinatorial display library by sequential magnetic bead enrichment and flow cytometry sorting. The Pacific Northwest National Laboratory (Richmond, Wash.) supplied most of the necessary reagents, protocols and a user manual used in this screening. Briefly, the procedure involved adding a mixture of the biotinylated ghrelin peptides each at 100 nM final concentration, to $1 \times 10^{10}$ yeast in 10 ml of buffer. After incubation to allow binding to the surface-expressed scFv, the yeast were washed 3 times and resuspended in 5 ml buffer with streptavidin-labeled magnetic microbeads. This allowed for the isolation of yeast expressing ghrelin-reactive scFv using a Miltenyi LS magnetic column (Miltenyi Biotec Inc., Auburn, Calif.). The isolated clones were grown overnight and subjected to a second round of magnetic selection.

Those 2× magnetically enriched ghrelin-binding yeast were then more stringently selected by a process of 2× flow cytometric sorting after reaction with the biotinylated ghrelin peptides and a red fluorescent streptavidin detection reagent. A green fluorescent c-myc probe was also added to show scFv expression on the yeast. Sorted yeast having both red and green labels appear in the upper right quadrant, and these were collected. This iterative sorting process was performed to obtain a full collection of ghrelin-binding clones. After plating on agar, each individual epitope-specific clone was picked off the plate, grown up in selective media, and then induced to express its surface scFv. The epitope specificity for these isolated clones was defined using the flow cytometer to test its binding to the ghrelin peptides panel.

Figure 4A:
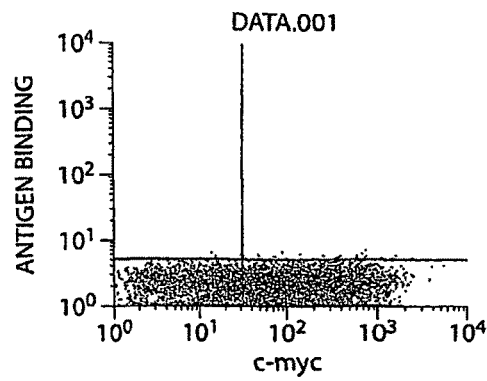
FIG. 4 shows the results of the flow cytometry of an anti-ghrelin yeast clone. No ghrelin (FIG. 4A); +$G_{1-5}$biotin (FIG. 4B); +$G_{1-28}$biotin (FIG. 4C).
Figure 4B:
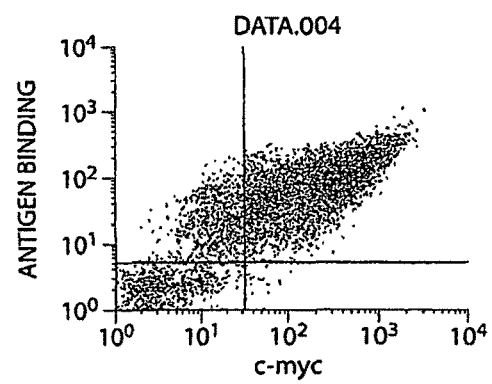
Figure 4C:
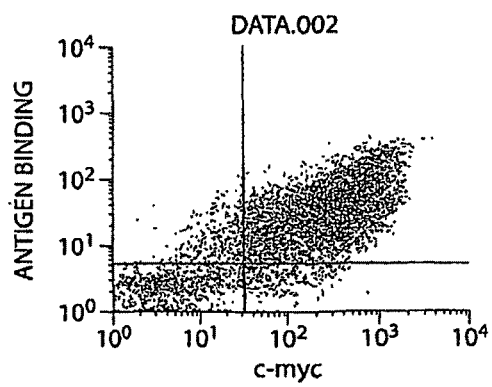

The flow cytometric pattern given by one of the 14 anti-ghrelin yeast clones isolated is shown in FIG. 4. FIG. 4A shows that the clone after reaction with the scFv probe (an anti-c-myc antibody) alone displays an increased green fluorescence shift along the abscissa representing scFv expression on the yeast surface. FIG. 4B shows that the clone gives an additional red fluorescence shift along the ordinate after binding to the small biotinylated Peptide, $G_{1-5}$biotin, plus red fluorescent streptavidin. The red shift in panel FIG. 4C similarly demonstrates that the scFv on this clone also binds the full-length ghrelin-biotin peptide, $G_{1-28}$biotin.

Multiple anti-ghrelin clones that react with both $G_{1-5}$biotin and $G_{1-28}$biotin have been isolated. Some clones that bind exclusively to the $G_{1-28}$biotin but not to $G_{1-5}$biotin have also been isolated. These likely recognize sequence epitopes of ghrelin beyond the 1-5 region and/or conformational determinants. Binding was highly specific for ghrelin since there was no red shift after reaction of those clones with numerous biotin peptides unrelated to ghrelin. Other human anti-ghrelin scFv antibodies that can be used as therapeutic agents for the treatment of obesity can be gleaned from this and/or other libraries.

Production of Single Chain Fv Antibodies

DNA encoding anti-ghrelin scFv antibodies expressed by the surface expression yeast chines was transferred into the pPNL9 secretion vector (part of a kit from Pacific Northwest National Laboratories, Richmond, Wash.). S. cerevisiae YVH10 yeast cells (also part of a kit from Pacific Northwest National Laboratories) were used for scFv production and purification. P. pastoris yeast cells have also been used. Using PCR the scFv DNA from individual surface expression yeast clones was obtained and utilized to transform the YVH10 secretion strain. The ~700 bp bands obtained by agarose gel electrophoresis are the appropriate size for the scFv gene. This DNA was inserted into the secretion vector by gap repair cloning. Following transformation and selection on agar plates, the YVH10 yeast clones were grown in induction medium so that each individual anti-ghrelin scFv antibody could be produced and isolated. The pPNL9 secretion vector of S. cerevisiae YVH10 cells was used, as it allows for purification through the 6-His tag. The anti-ghrelin scFv antibody production was induced by the galactose/raffinose/dextrose media. Typically, pure scFv is obtained at a 2 mg/L yield under standard conditions, O.D.$_{600}$~3/ml. However, with a New Brunswick BioFlo IV high capacity fermenter (New Brunswick Scientific, Edison, N.J.) with pH and $O_2$ monitoring and control, yeast can be grown to an O.D.$_{600}$~500/ml so that much greater yields of anti-ghrelin scFv is attainable.

During growth in induction medium, scFv produced by S. cerevisiae YVH10 yeast is secreted into the media. Since the yeast do not have to be lysed, large amounts of cytoplasmic protein are not released and high-grade purification of the scFv is easy to perform. This was accomplished by binding to a nickel column (Qiagen Ni-NTA affinity column, Qiagen, Valencia, Calif.) via its 6-His tag. The column was washed, and the bound anti-ghrelin scFv was released using 200 mM imidazole. The imidazole was removed, and the scFv concentrated on an Amicon micro-concentrator (Millipore, Billerica, Mass.). Media from 1-4 liter fermentation batches was concentrated and exchanged with PBS using a Centramate tangential flow ultra-filtration apparatus (Pall Corporation, East Hills, N.Y.) before application onto the Ni-NTA column. ScFv purified in this manner gives one prominent single band on SDS-PAGE.

Characterization of the Anti-Ghrelin Monoclonal and Single Chain Fv Antibodies

Binding Specificity

The binding specificity of the antibodies to full-length ghrelin, its small peptide epitopes and to the octanoyl transition state analog using a comparative ELISA method was examined. A ghrelin peptide of interest was adsorbed directly onto a microtitre plate followed by blocking with bovine serum albumin (BSA). The serum, monoclonal or scFv antibody was allowed to react and after washing, it was exposed to, for example, peroxidase-labeled anti-mouse gamma specific or anti-human lambda/kappa light chain specific antibodies. After a final wash, a chromogenic substrate was added to develop the color, which was quantified on a microplate reader.

ELISA data was obtained with the above method from monkey sera (Tables 1 and 2) as well as from several purified monoclonal antibodies. Table 3 shows the raw ELISA data for a titration of one of the purified anti-$G_{1-5}$ monoclonal antibodies (5010) when tested against three ghrelin peptides. This antibody, which is directed against the amino end of ghrelin, cross-reacts with the full-length molecule, $G_{1-28}$. It also binds to a $G_{1-5}$ peptide that is missing the octanoyl group on the second serine, which indicates that the 5G10 monoclonal antibody does not predominantly recognize that structural moiety. Some of the other anti-$G_{1-5}$ antibodies required this octanoyl moiety for strong binding. Exclusive interaction with the biologically active form of ghrelin can improve therapeutic efficacy.

TABLE 3

ELISA to Measure Binding of an Anti-$G_{1-5}$ Monoclonal Antibody
ELISA READING (O.D. 450 nm)

| Adsorbed to Plate | 5G10, 0M | 5G10, $10^{-9}$M | 5G10, $10^{-8}$M | 5G10, $10^{-7}$M |
|---|---|---|---|---|
| G1-5 | 0.388 | 0.379 | 1.267 | 2.903 |
| G1-28 | 0.504 | 0.333 | 0.944 | 3.069 |
| G1-5, no octanoyl | 0.178 | 0.225 | 0.716 | 2.741 |

Figure 5:
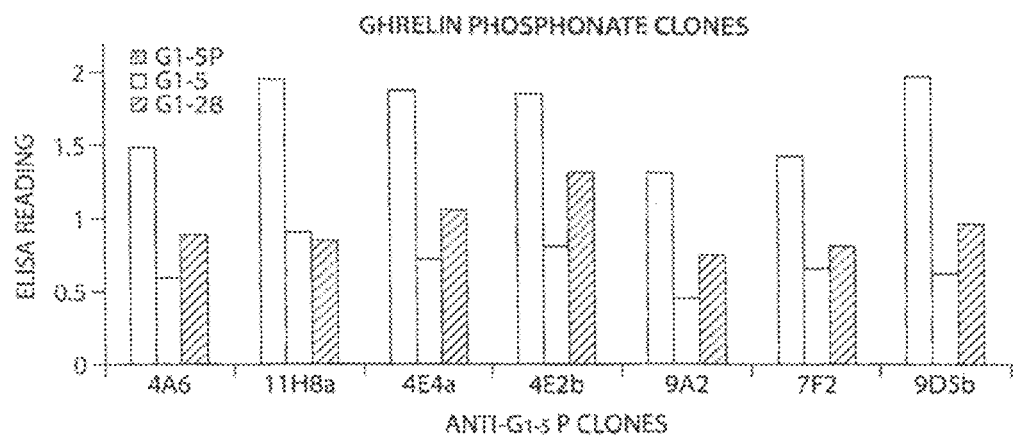
FIG. 5 indicates the specifity of anti-ghrelin transition state analog antibodies.

A similar ELISA assay was used to test the specificity of some of the purified monoclonal antibodies directed against the ghrelin transition state analog, $G_{1-5}$P. Those antibodies bound preferentially to the immunizing peptide $G_{1-5}$P but cross-reacted with both the $G_{1-5}$ and $G_{1-28}$ peptides, having the naturally occurring octanoyl ester (FIG. 5). Table 4 also provides data demonstrating the octanoyl specificity of various monoclonal anti-ghrelin antibodies that were produced.

TABLE 4

Octanoyl-Specificity of Different Monoclonal Anti-Ghrelin Antibodies
ELISA READING (O.D. 450 nm)

| Monoclonal Antibody | Peptide Adsorbed to Plate | |
|---|---|---|
| | G1-5 | G1-5, no octanoyl |
| 10D8 | 1.515 | 0.451 |
| 5C6 | 1.842 | 1.888 |
| 5G10 | 2.903 | 2.741 |
| 9F12 | 0.525 | 0.463 |

A radioimmunoassay has also been developed using commercially available $^{125}$I-labeled $G_{1-28}$ and a polyethelene glycol method for the separation of antibody-bound $^{125}$I-ghrelin versus free $^{125}$I-ghrelin. The label is on the histidine at position 9 in the ghrelin molecule (FIG. 2), and iodination can be performed, for example, with the method provided in Tsomides et al. (Tsomides, T. J., and Eisen, H. N. 1993. *Anal. Biochem.* 210: 129-135.) This test allows for the measurement of relative binding affinities of anti-ghrelin antibodies and can also be used in a competitive displacement assay for the measurement of unlabeled ghrelin in biological samples.

Figures 6A, 6B, 6C:
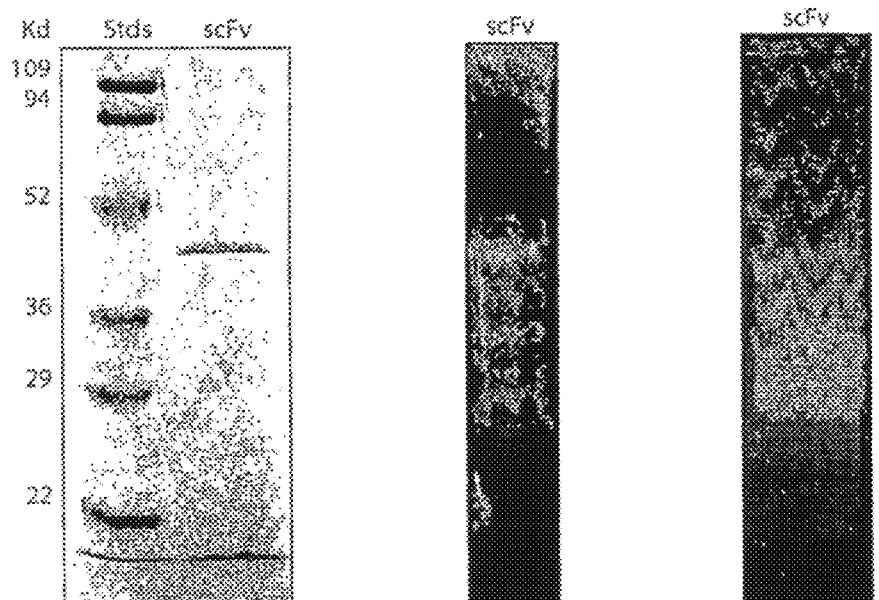
FIG. 6 provides the results of a PAGE experiment with a scFv antibody: protein stain (FIG. 6A); in-gel Western of ghrelin binding (FIG. 6B); and V5 Tag (FIG. 6C).

To initially characterize the nickel-NTA column-purified anti-ghrelin scFv antibodies an in-gel western detection protocol was used. Subsequent to polyacrylamide gel electrophoresis (PAGE), ghrelin binding to the scFv was demonstrated by using biotin-labeled ghrelin followed by a red fluorescent streptavidin secondary reagent (FIG. 6B). The V5 tag on the anti-ghrelin scFv was detected using a goat anti-V5 followed by a green fluorescent anti-goat IgG secondary antibody (FIG. 6C). Fluorescently-labeled protein bands were visualized using an Odyssey infrared imaging system (LI-COR Biosciences, Lincoln, Nebr.). For comparison, a gel of the purified anti-ghrelin scFv that was Coomassie-stained for protein (FIG. 6A) is also shown. The band position corresponds to a molecular weight range expected for scFv species that are glycosylated to different extents in yeast.

Anti-ghrelin scFv antibodies obtained after PAGE can be transferred onto a membrane. An Edman degradation sequence analysis of the major protein band can then be performed. The first 10 amino acids of the sequence should match the HA tag plus linker that would be expected for the amino terminus after secretion of the scFv molecule. The amino terminus of the scFv prior to its secretion into the medium begins with an alpha prepro leader sequence. The leader, which is removed upon secretion, is directly followed by an HA tag sequence (YPYDVPDYA (SEQ ID NO: 25)) and its linker (GGGGS (SEQ ID NO: 26)) to the subsequent variable heavy chain region of the scFv. The sequence data can demonstrate unequivocally that designated human scFv antibodies have been produced. This analysis scheme can be used to verify scFv antibodies having a different specificity.

Microcalorimetry

The underlying thermodynamic interactions between ghrelin peptides and the anti-ghrelin monoclonal or scFv antibodies can be studied using microcalorimetry (e.g., isothermal titration calorimetry and differential scanning calorimetry.) An isothermal calorimetric binding titration can be obtained using an instrument that automatically injects small aliquots of a ghrelin peptide into the stirred antibody solution while measuring the heat generated by their binding interaction. A calorimetric binding titration and binding curve is produced by a computer program interface. The association constant, Ka, the enthalpy, $\Delta H$, and the entropy, $\Delta S$, are all calculated from this data. Measurement of the association constants for different anti-ghrelin monoclonal and scFv antibodies provide a direct comparison of their different affinities for the hormone. Differential scanning calorimetry will provide the heat capacity ($\Delta Cp$) of reaction and measure conformational energy and thermal transitions. These binding parameters help to reveal what kinds of intermolecular interactions contribute to the reaction between each ghrelin epitope and its particular anti-ghrelin monoclonal or scFv antibody.

Figure 14:
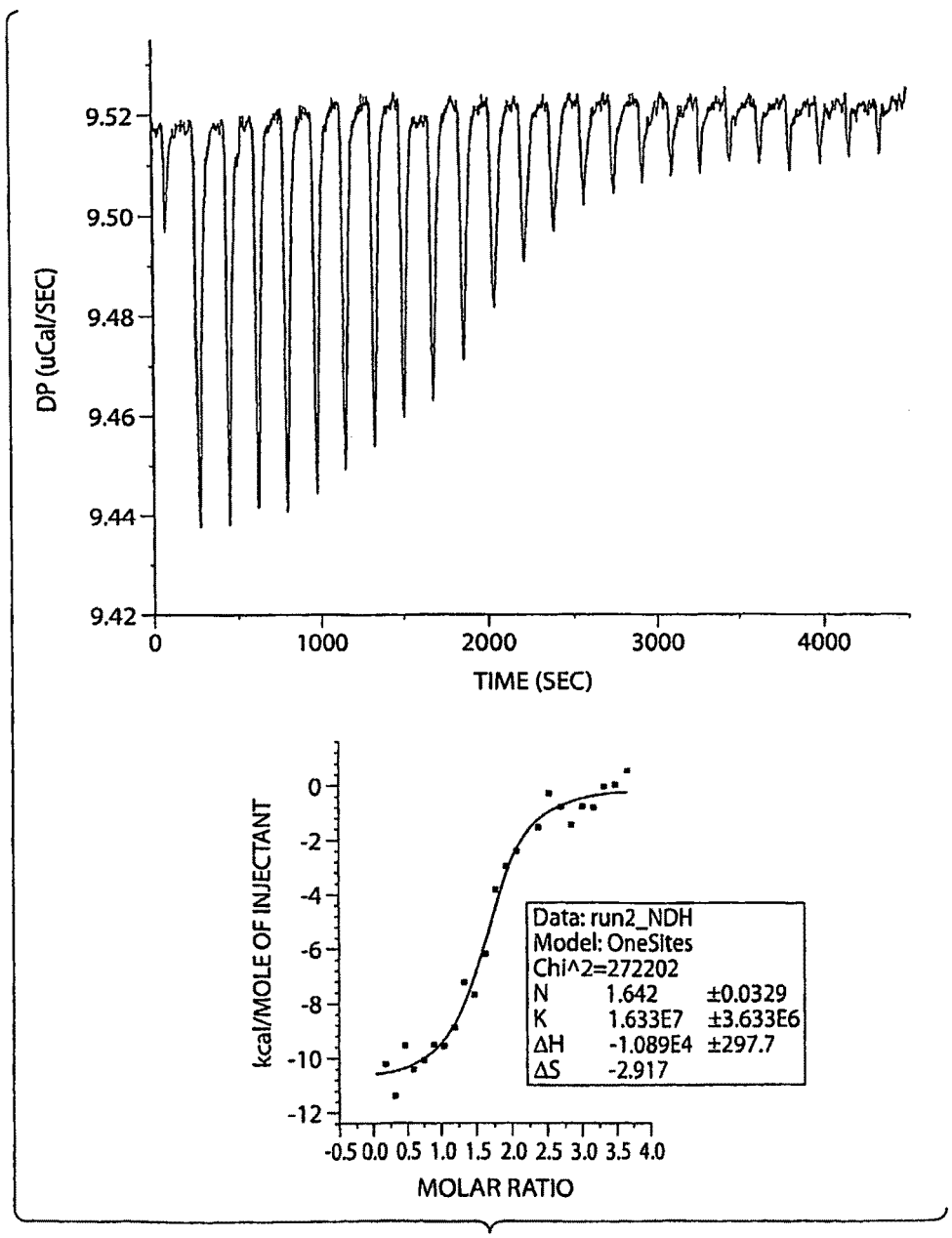
FIG. 14 provides results from an isothermal calorimetric binding titration that was performed with a monclonal anti-beta amyloid antibody and the beta amyloid peptide epitope that it recognizes.

Information regarding antibody binding of ghrelin can be obtained with a surface plasmon resonance instrument (Biacore Life Sciences, Piscataway, N.J.), which measures binding kinetics and can be used to determine individual rates constants of association (ka) and disassociation (kd). As an example, FIG. 14 provides results from an isothermal calorimetric binding titration that was performed with a monclonal anti-beta amyloid antibody and the beta amyloid peptide epitope that it recognizes. Binding was exothermic with ka=$1.6 \times 10^7$ M$^{-1}$, $\Delta H$=$-11$ kcal and $\Delta S$=$-3$ cal/mole/deg.

Cleavage

Some monoclonal and scFv antibodies, such as those directed against the ghrelin analogs like the transition state analog peptide $G_{1-5}P$, can hydrolytically cleave the octanoyl moiety from native ghrelin and render the hormone inactive. Therefore, an assay to evaluate the antibody-mediated hydrolysis of the octanoyl ester of ghrelin was developed.

Figure 7:
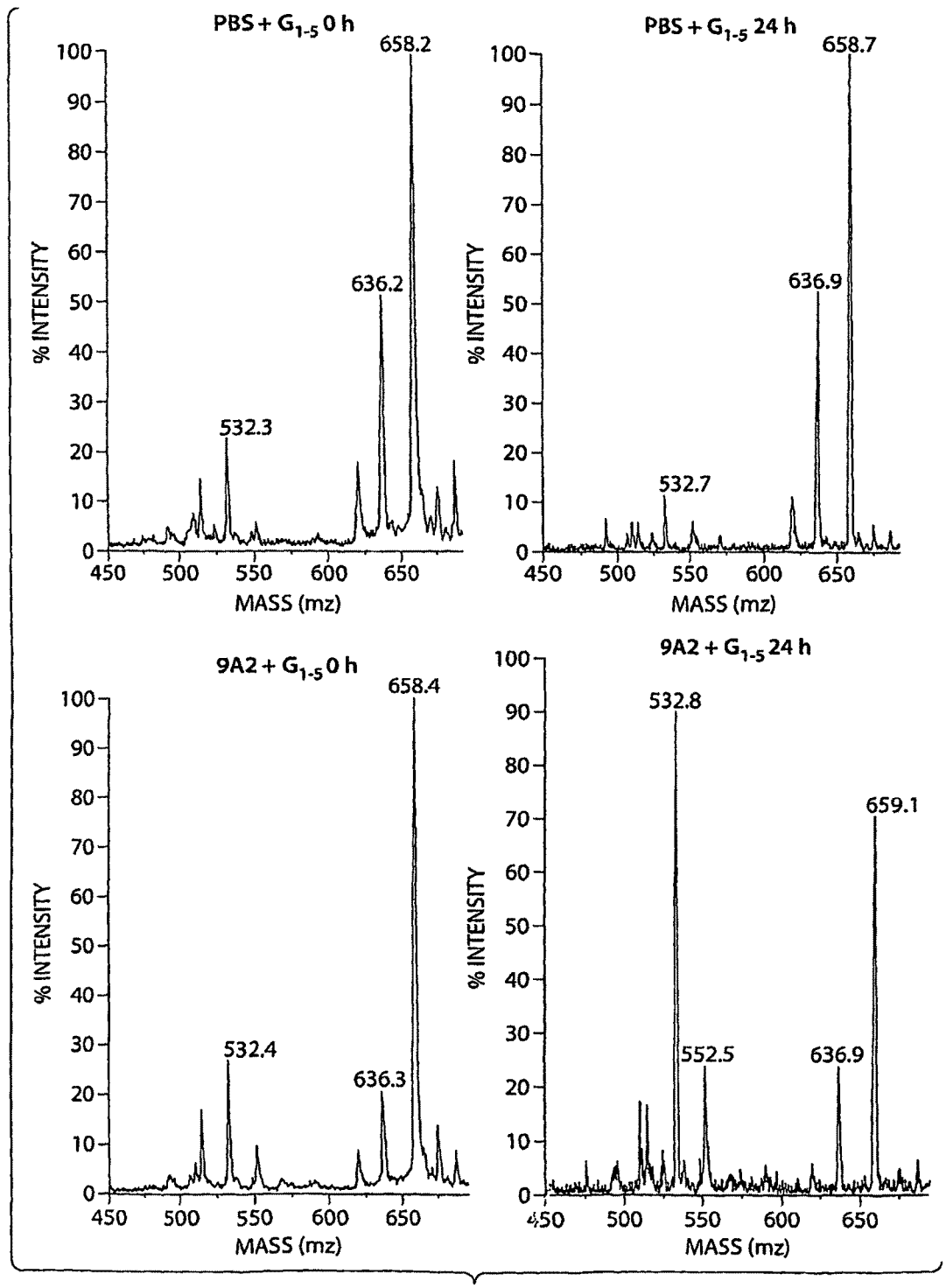
FIG. 7 provides the results of a mass spectral assay detecting the hydrolytic cleavage of the octanoyl group from $G_{1-5}$.

Mass spectroscopy was used to detect the conversion of octanoylated $G_{1-5}$ into $G_{1-5}$ containing no octanoyl group (they differ by 126 mass units.) A reaction mix was set up to contain $6.76 \times 10^{-11}$ moles of the 9A2 monoclonal anti-$G_{1-5}P$ antibody (FIG. 5) plus $390 \times 10^{-11}$ moles of $G_{1-5}$ in a volume of 2.5 µl PBS. The control contained $G_{1-5}$ alone in PBS. The two sealed tubes were incubated at 30° C., and 0.5 µl samples were removed at different intervals for analysis by MALDI-TOF mass spectrometry. Two time points from that assay are shown in FIG. 7.

At time zero both the PBS control and 9A2 reaction contained major peaks at 636 and 658 which correspond to $G_{1-5}$ and its Na$^+$ (+22) adduct. The 532 peak seen in both is the Na$^+$ adduct of $G_{1-5}$ without the octanoyl group. After 24 hours at 30°, the control remained virtually unchanged while the 9A2 antibody caused a simultaneous reduction in the amount of $G_{1-5}$ (659 peak) and an increase in the Na$^+$ adduct of hydrolysed $G_{1-5}$ (532). The identity of the 552 peak that also increased is unknown.

Examination of additional time points from this experiment indicated that the conversion of octanoylated $G_{1-5}$ to $G_{1-5}$ without the octanoyl group was progressive. Moreover it was calculated that the antibody exhibited turnover, each of its combining sites converting ~30 $G_{1-5}$ molecules in the 24 hr time span. The rate of hydrolysis for 9A2 is slow when compared to an enzyme, but even low levels of catalysis can be effective for eliminating active ghrelin from the blood.

Figure 8A:
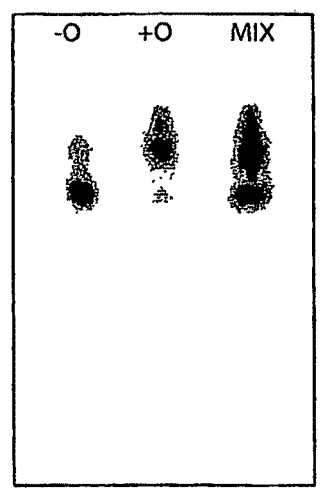
FIG. 8 provides the results of a TLC separation of octanoylated and non-octanoylated $^{125}$I-labeled $G_{1-10}$ (FIG. 8A).
FIG. 8B shows the results of the TLC separation following incubation with antibodies. Lanes 1 and 2 show non-octanoyl-$^{125}$I-$G_{1-10}$ and octanoyl-$^{125}$I-$G_{1-10}$, respectively. Lanes 3-8 show the effect of incubating the $^{125}$I-labeled $G_{1-10}$ octanoylated substrate with six protein A-purified anti-$G_{1-5}P$ transition state analog monoclonal antibodies. All were incubated for 2.5 h at 30° C. in PBS with EDTA to inhibit metallopeptidases.
Figure 8B:
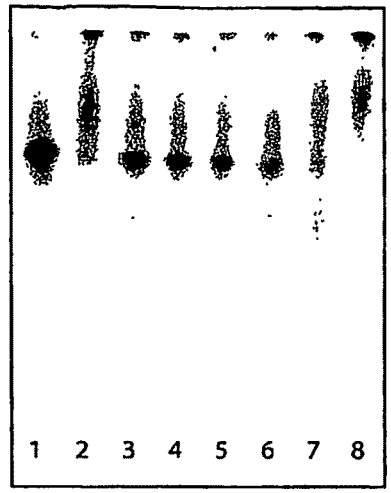

A high throughput assay for ghrelin hydrolysis was also developed. A $^{125}$I-labeled $G_{1-10}$ peptide was synthesized and purified, and a $^{125}$I-labeled $G_{1-28}$ probe was obtained commercially (Amersham Biosciences Corp., Piscataway, N.J.). These radioactive substrates combined with thin layer chromatography (TLC) to separate the octanoyl and non-octanoyl ghrelin peptides (e.g., when run on a silica gel C18 reverse phase thin layer plate using an acetonitrile/$H_2O$/TFA solvent) provide a method to easily monitor ghrelin esterase activity. Ghrelin spots were initially detected with ninhydrin. FIG. 8 shows the separation of octanoylated $^{125}$I-labeled $G_{1-10}$ and non-octanoylated $^{125}$I-labeled $G_{1-10}$ on a cellulose TLC plate developed with n-butanol/acetic acid/water/pyridine at a vol/vol ratio of 15/3/12/10, respectively. A phosphorimager was used to facilitate the detection of radiolabeled spots on the TLC plate. These preliminary results suggest that several of the antibodies cleaved the octanoyl group from ghrelin (Lanes 3-6) while others did not (Lanes 7 and 8).

Active and Passive Vaccination for Quelling Hunger in Mice

Figure 9:
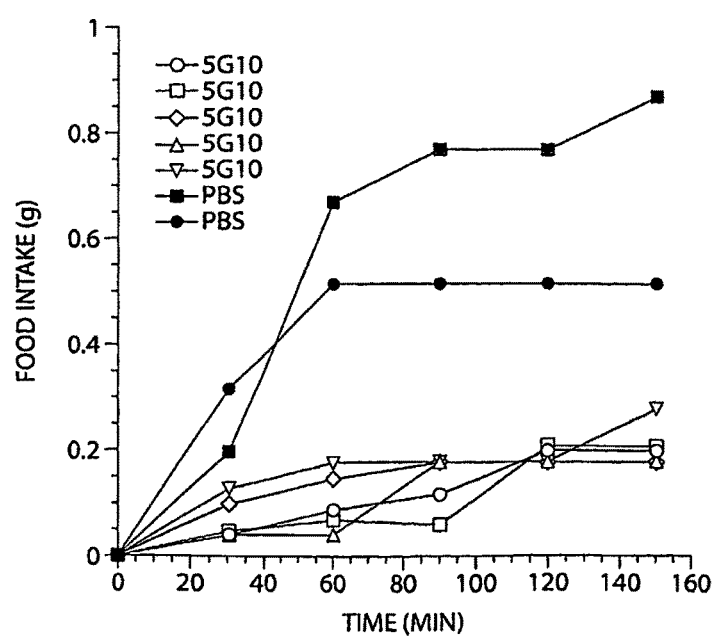
FIG. 9 indicates the food consumption after passive vaccination with an anti-ghrelin antibody.
Figure 10:
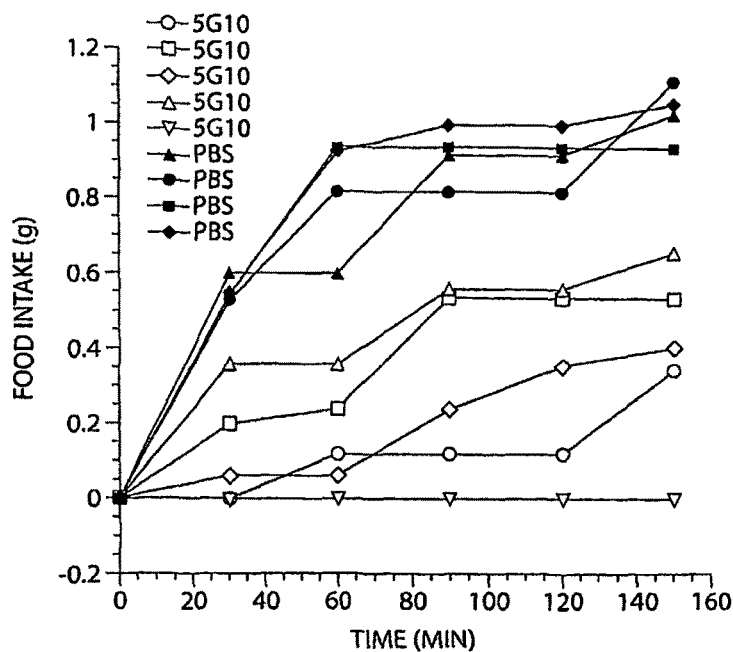
FIG. 10 indicates the food consumption after passive vaccination with an anti-ghrelin antibody.
Figure 11:
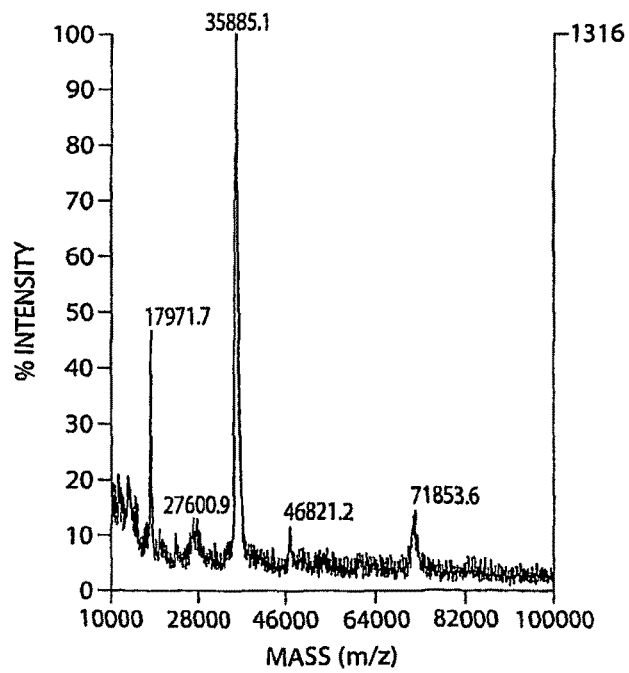
FIG. 11 provides the mass spectrum of G1 scFv.
Figure 12:
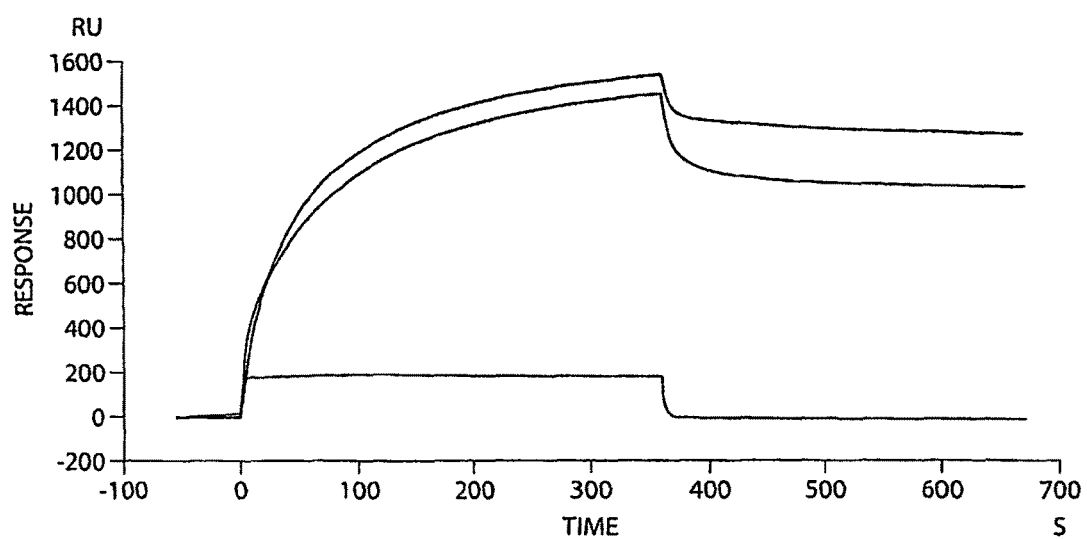
FIG. 12 provides a sensorgram for the G1 interaction with non-octanoylated $G_{1-5}$ (bottom line), $G_{1-5}$ (top line) and $G_{1-28}$ (middle line).

The 5G10 anti-$G_{1-5}$ monoclonal antibody was used to evaluate the effect of a passively administered antibody on the hunger response in mice. C57BL/J test mice, 6-10 weeks old, that had been fed ad libitum were fasted overnight to naturally stimulate ghrelin secretion. In the morning they were injected i.p, with either 0.3 ml of 5G10 (4 mg) in PBS or 0.3 ml PBS alone. Three hours later they were given a weighed pellet of food. The pellet was weighed again at 30 min time intervals to monitor food intake. FIG. 9 illustrates the time course of cumulative food intake for 5 experimental and 2 control mice. At both the 30 min and 60 min time points, mice that had received 5G10 ate less than the control animals. Eating subsided after 150 min during which the controls had consumed ~0.5 g and 0.8 g of food while the vaccinated mice had eaten only ~0.2 g. This 0.3 g-0.5 g differential is high for mice, since by comparison on a weight-to-weight basis it would correspond to a person eating 2-3 pounds more food. The experiment was repeated with 5 experimental and 4 control mice using similar conditions (FIG. 10). In this case there was greater variability for the food consumption pattern of the 5G10-treated mice, but it was still suppressed compared to the PBS controls. One vaccinated mouse did not eat during the 150 min interval but resumed eating during the night. Additional variations in experimental design can be examined to find the most favorable for demonstrating hunger suppression and weight loss. For example, instead of being fed ad libitum, mice can be given food for only an hour in the morning and at night. In this way, the mice can develop a more human-like conditioned response to ghrelin stimulation. This conditioning might enhance their response to ghrelin and make it more consistent.

For the experiments described above, the presumption was that the administered anti-ghrelin antibody sequesters ghrelin in the blood stream and prevents its passage into the brain and thereby causes hunger suppression. Controls can be used to confirm this. For example, a control mouse monoclonal antibody that is isotype matched to 5G10 (IgG 2b) but does not bind ghrelin can be isolated. Such an antibody can be used in place of PBS control injections. Another specificity control can be the use of non-octanoylated $G_{1-5}$ as an inhibitor of antibody binding. This peptide, as well as others (e.g., $G_{1-5}P$) binds to 5G10 (Table 3) but has no ability to elicit a hunger response. It, therefore, can be added to an antibody mixture in a 30-fold excess over the antibody binding sites just prior to injecting the mixture into mice. This will effectively block the ability of an antibody (e.g., 5G10) to bind full-length ghrelin in the fasted mice and, thereby, should prevent the antibody from suppressing the hunger response compared to unblocked 5G10. Such peptides, therefore, can be used as a control to show that appetite suppression is due to an administered antibody. Control animals can also be vaccinated with a KLH antigen that will elicit antibodies that do not bind ghrelin. Such animals should have a normal unsuppressed hunger response.

Long-term studies can be performed to see if anti-ghrelin antibody treatment affects the pattern of weight gain in mice. Studies with the ghrelin knock-out mice suggest that there should be little or no effect on weight gain in normal mice (Wortley, K. E., et al, 2004. Proc Natl Acad Sci USA 101: 8227-8232; Sun, Y., at al. 2003. Molec and Cellular Biol 23:7973-7981.) However, different groups of C57BL/J mice can be injected twice a week i.p. with 100 µg of either a specific anti-ghrelin monoclonal, scFv antibody or an appropriate non-specific control antibody. This should maintain adequate anti-ghrelin antibody levels over a period of time. ELISA can then be used to measure the actual serum antibody titers. The two groups of mice can then be monitored for food consumption and weight gain or loss.

Mice also respond to i.p. injection of synthetic ghrelin by showing an increased uptake of food (Wang, L., et al. 2002. Neurosci Lett 325: 47-51.) The experiments described above, which test the effects of anti-ghrelin antibodies on the hunger response, can be repeated using exogenous stimulation with the injected hormone in place of its natural production via fasting. This strategy can give further control over the timing of the hunger response.

A radiolabeled $^{125}$I-labeled $G_{1-28}$ probe can be obtained commercially and co-injected with ghrelin so that anti-ghrelin antibody bound versus free fractions of hormone in the blood of experimental mice can be assessed. A polyethylene glycol separation method or anti-antibody capture method can be used to distinguish those bound and free fractions. Blood and brain samples can be collected within 10 min to avoid extensive breakdown of the $^{125}$I-labeled $G_{1-28}$ peptide (Banks, W. A., et al. 2002. J Pharmacol Exp Therapy, 302: 822-827.)

Plasma immunoreactive ghrelin levels can be measured by radioimmunoassay, such as one that uses $^{125}$I-labeled $G_{1-28}$ and rabbit polyclonal anti-ghrelin antibodies (Cummings, D. E., et al., 2003. N Engl J Med 346:1623-1630; Cummings, D. E., et al., 2001. Diabetes 50: 1714-1719.) Such a radioimmunoassay can be used to measure ghrelin levels in a subject before and after treatment with an anti-ghrelin antibody or other vaccine. Appropriate controls can be used to ensure that the anti-ghrelin antibodies in the plasma do not interfere with the assay. Antibody-bound ghrelin can be removed before assaying for free unbound ghrelin levels.

To test the ability of endogenous anti-ghrelin antibodies for quelling hunger, separate groups of C57BL/J mice can be vaccinated with different ghrelin antigens, such as, for example, $G_{1-5}$, full-length ghrelin and/or the ghrelin phosphonate transition state analog linked to KLH. Immunization can be accomplished by i.p. injection with 50 µg of the ghrelin antigen(s) or a non-specific control peptide linked to KLH. Each can be initially injected emulsified in complete Freunds adjuvant, followed optionally by a second and/or third course in incomplete Freunds adjuvant. Thereafter, the mice will be periodically boosted with an appropriate antigen in incomplete Freunds adjuvant. This protocol can maintain adequate anti-ghrelin antibody levels for a long period of time. Animals displaying high titer anti-ghrelin antibodies with appropriate specificity can be used in subsequent studies to determine anti-ghrelin antibody dependent suppression of appetite.

Comparison of the Effectiveness of Binding versus Catalytic Antibodies

A comparison of conventional anti-ghrelin binding antibodies versus catalytic anti-ghrelin antibodies can be performed. An anti-ghrelin binding antibody found to be effective in suppressing a hunger response and a catalytic anti-ghrelin antibody can be tested on an equimolar basis in a mouse hunger suppression assay. Blood levels of active and inactive ghrelin can also be determined. These data should indicate if improved therapeutic results can be obtained with an antibody that catalytically inactivates ghrelin as opposed to sequestering it in the blood stream via binding.

Refining Antibodies for Therapeutic Use

Standard molecular manipulations can be use to engineer higher affinity antibodies that bind a greater amount of the ghrelin in the blood and/or can be administered at a much lower dose to achieve the same level of hunger suppression as a lower affinity antibody. An antibody gene of interest can be engineered to increase antibody affinity, bestow bivalency and even create bispecific scFv dimers that can cross the blood brain barrier via transcytosis.

For instance, mutagenic PCR can be used to evolve anti-ghrelin antibodies, such as scFv antibodies, toward higher binding affinities and greater functionality. The protocol for creating mutagenized libraries is clearly laid out in the Pacific Northwest National Laboratory's user's manual. Briefly, for molecular evolution, the anti-ghrelin scFv DNA is amplified using error-prone PCR to incorporate 3 to 7 point mutations/scFv. The material is then cloned into a surface expression vector using the endogenous homologous recombination system present in yeast, known as "Gap-Repair". This allows mutated libraries of $1\text{-}10 \times 10^6$ clones to be rapidly generated and screened. The screening involves 3 to 4 rounds of flow cytometry sorting for clones that bind the appropriate ghrelin peptide at 10-fold higher affinity relative to the parental clones. Typically the mutagenized yeast are reacted with a biotin-ghrelin peptide at a concentration that is $\frac{1}{10}^{th}$ the Kd of the parental clone. The sample is then sorted on the flow cytometer, and the brightest 0.2% of the fluorescent population is selected as high affinity anti-ghrelin scFv antibody clones.

Mutagenic PCR can also be used to generate catalytic anti-$G_{1-5}P$ scFv antibodies with an increased turnover number ($k_{cat}$) for cleaving the octanoyl group from ghrelin. This genetic maneuver improves the probability that a side chain that facilitates acid/base catalysis into the active site of an scFv with only rudimentary activity is introduced, thereby enhancing its $k_{cat}$. The new catalytic antibodies can be expressed on the surface of yeast and be sequentially sorted for binding to ghrelin by flow cytometry at both 0° C. and 37° C. The low temperature prevents cleavage. The fraction that binds ghrelin can then be collected. The ghrelin-positive yeast can then be incubated at 37° C. so that catalytic cleavage can proceed, and the bound ghrelin is released. On a subsequent cell sort, only the ghrelin-negative catalytic yeast could be collected. The catalytic activity of the new mutagenized scFv yeast can be compared to that of the parental clone so that any substantial improvements in $k_{cat}$ can be identified.

The antibodies can also be structurally modified to achieve bivalent binding, a prolonged serum half-life or passage into the CNS. There are several different approaches that can be taken to create homo- or hetero-dimers, and each has special advantages as well as disadvantages. For instance, a carboxyl-terminal $Gly_4Cys$ linker moiety can be added to a scFv antibody (Huston, J., et al. 1994. *Cell Biophys.* 24-25: 267-278; Adams G., 1993. *Cancer Res.* 53: 4026-4034). The Cys thiol is stabilized and Ellman's reagent (E) is used to activate this group on one of the scFv components, so that it will react unidirectionally with the second via disulfide exchange. This is illustrated in Equation 1 below.

$$Fv_A\text{-SH}+Fv_B\text{-SS-E}\rightarrow Fv_A\text{-SS-}Fv_B\text{+E-SH} \quad \text{(Equation 1)}$$

This approach can be used to make disulfide-linked scFv bivalent dimers or heterobispecific dimers, $Fv_A$-SS-$Fv_B$ (50 kDa). If $Fv_A=Fv_B$ then a bivalent $(Fv)_2$ anti-ghrelin antibody will be created. If $Fv_A$ is anti-ghrelin and $Fv_B$ is directed against a receptor expressed on brain capillary endothelial cells (e.g., transferrin or insulin receptor) then a bispecific antibody that can cross the blood-brain barrier via transcytosis will result. This would allow an anti-ghrelin scFv antibody to come into direct contact with ghrelin in the CNS, block its interaction with receptors and thereby facilitate hunger suppression. The antibody can also be a full-sized antibody. A Cys linker can also be used as a point of attachment for creating conjugates with other biomolecules that would, for example, prolong the serum half-life of the anti-ghrelin antibody (e.g., thioether-linked polyethylene glycol, albumin or albumin-binding peptide.) (Chapman, A. P., 2002, *Advanced Drug Delivery Rev.,* 54:531-545; Dennis, M. S., et al., 2002, *Journal Biological Chemistry,* 277:35035-35043). For example, the DNA sequence (SEQ ID NO: 27) that encodes a linker plus an albumin binding peptide was added into a yeast pPLN9 secretion vector (Pacific Northwest National Laboratory). This was designed so that expression of any scFv antibody gene inserted into this vector will produce a scFv antibody that has that linker and albumin binding peptide appended to its carboxyl terminus. Thereby, the typical 1 hour half-life of an unmodified scFv can be prolonged to up to 19 days (the half-life of albumin in a human) by virtue of this integrated peptide binding to endogenous albumin in the circulation. Alternative diabody and mini-antibody strategies can also be utilized to prolong serum half-life.

Example 2

Human Anti-Ghrelin ScFv Antibodies and Hunger Response in Mice

The blocking effect of anti-ghrelin scFv antibodies on the hunger response of mice was evaluated. The immunoneutralization results are discussed in terms of whether the route of ghrelin to the brain is via the blood or vagus nerve.

Mouse monoclonal anti-ghrelin antibodies were initially used to demonstrate that immunological modulation of the hunger response is feasible. Further efforts have focused on producing ample amounts of human anti-ghrelin scFv antibodies in yeast. This could, if so desired, be a way of avoiding obtaining monoclonal antibody-containing ascites fluid from numerous mice. Three distinct anti-ghrelin scFv antibodies were prepared and designated as clone G1, G11 and G14. The mass spectrum shown in FIG. 11 reveals that the G1 scFv has a mass of 35,885 kDa. This exceeds its calculated size and indicates that ~5,000 mass units are due to glycosylation. Minor peaks for the doubly charged and dimer forms are also visible in the spectrum.

Biacore surface plasmon resonance technology was used to assess the specificity, binding kinetics and affinity of the clonal anti-ghrelin scFv antibodies. Various ghrelin peptides were attached to the sensor chip either by biotin binding to streptavidin or via thioether linkage through a terminal cysteine residue. A sensorgram that plots the resonance unit response against time is presented in FIG. 12. The sensorgram curves monitor the interaction of the G1 scFv with three different ghrelin peptides ($G_{1-5}$, non-octanoylated $G_{1-5}$ (octanoylated) and $G_{1-28}$). The first part of these curves represents scFv binding to the ghrelin peptides, and the second part represents its dissociation. The G1 scFv bound to both octanoylated forms but not to the peptide missing that modification. Thus the ghrelin epitope that G1 recognizes is proximal to its amino terminus and involves the octyl ester moiety at the second serine. Association/dissociation curves like those shown in FIG. 12 can be used to calculate affinity constants for the different anti-ghrelin scFv antibodies.

FIG. 13 shows the results of the first hunger response experiment following treatment with anti-ghrelin scFv antibodies. The protocol was slightly modified from that described for the monoclonal antibody tests. Mice were conditioned to fasting at night and eating during the day. Pretreatment consumption patterns were then monitored so that deviant animals (e.g., mouse A, FIG. 13 left) could be removed from the experimental cohort. The next morning after fasting, two mice were injected i.p. with either 0.3 ml of anti-ghrelin scFv antibody clone G1 (1.2 mg), G11 (2.4 mg) or G14 (0.765 mg) in PBS or with 0.3 ml PBS alone. One hour later food intake was monitored so that any scFv-mediated suppression of appetite could be detected (FIG. 13 right).

Figure 13:
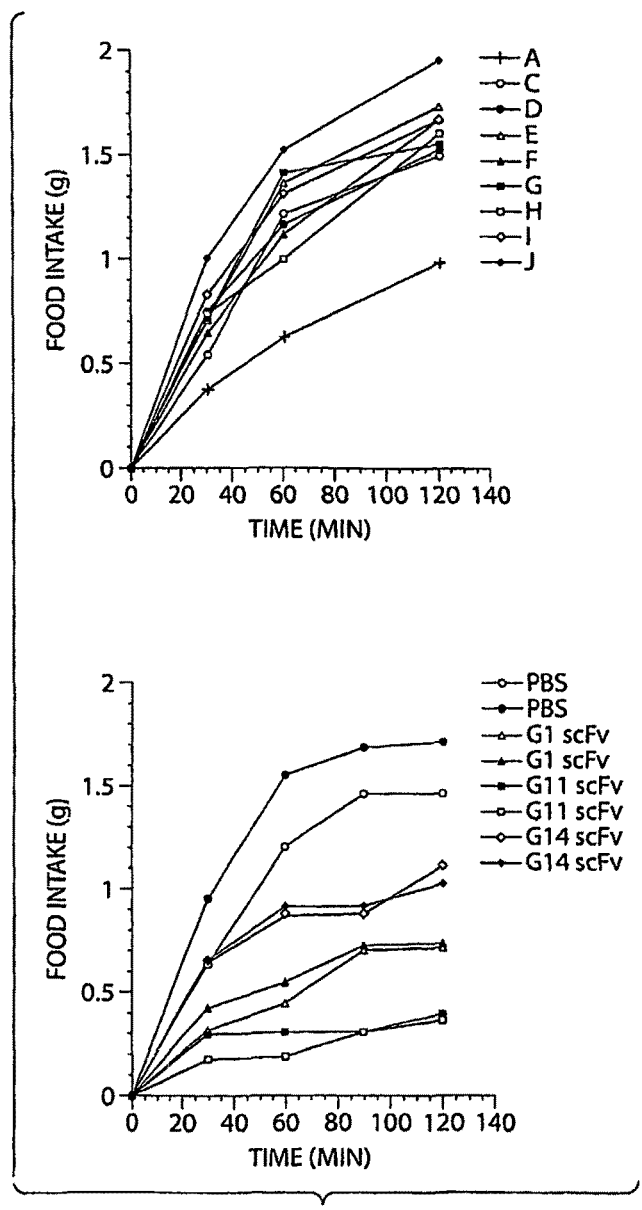
FIG. 13 indicates food intake 1 day prior to (left) and 1 hour after (right) anti-ghrelin scFv treatment.

Treatment with anti-ghrelin scFv antibodies produced a clear reduction of the initial food intake compared to the PBS control mice (FIG. 13 right). The results are strengthened by the fact that all mice were acclimated and eating at the same rate the day prior to treatment (FIG. 13 left). The extent of appetite suppression appeared to vary for the three clonal scFv agents used (FIG. 13 right). However, since those differences are proportional to the dose injected they may simply reflect higher scFv levels in the animals.

Measurements beyond 120 min indicated that the rate of eating between control and treated mice gradually normalized over time. Interestingly, slight residual appetite suppression was noted in the G11 treated mice after fasting again overnight and retesting their food consumption in the morning without further scFv treatment. Additional tests have been designed to determine if the ghrelin blockade was eased because of scFv elimination, e.g., by regulating periodic scFv treatment during the day to prolong its effect. Alternatively, the eating may have simply resumed in a ghrelin independent mode similar to the basal type eating that was observed in ghrelin knockout mice where stimulation by ghrelin was precluded.

The fact that human anti-ghrelin scFv antibodies suppressed hunger in mice further confirms the results of the experiments with mouse monoclonal anti-ghrelin antibodies. The two agents were derived from dissimilar sources, mouse ascites fluid versus yeast induction medium. The were also purified differently, using protein A versus nickel affinity chromatography. In addition, substantial size differences exist between the monovalent scFv antibody (36 kDa) and bivalent whole antibody (150 kDa). However, despite all of these distinctions, the two types of anti-ghrelin antibodies are very similar in their ability to modulate the hunger response using the mouse model.

The vagus nerve can play an important role in the transmission of ghrelin's hunger signal to the brain, since intravenously injected ghrelin failed to induce feeding when that nerve was severed (Date, Y., et al. 2002. *Gastroenterology* 123:1120-1128.) Anti-ghrelin antibodies, therefore, can block ghrelin action by intercepting ghrelin in the blood stream and preventing its passage across the blood-brain barrier and/or they can function by blocking ghrelin stimulation of the vagus nerve, perhaps before it reaches vagal afferent terminals which innervate the stomach. To distinguish between the two possibilities the inhibitory effectiveness of anti-ghrelin antibodies as a function of the mode of injection can be measured. Blockage of blood-brain barrier passage may be favored by an i.v. injection route, while i.p. administration might better affect a vagal blockade mechanism.

Each of the foregoing patents, patent applications and references that are recited in this application are herein incorporated in their entirety by reference. Having described the presently preferred embodiments, and in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims.

I claim:

1. An isolated monoclonal antibody or antigen-binding fragment thereof that preferentially binds the ghrelin transition state analog, cross reacts with octanoylated native ghrelin, and cleaves octanoylated native ghrelin.

2. A composition comprising the isolated antibody of claim 1 or antigen-binding fragment thereof and a pharmaceutically acceptable carrier.

3. The composition of claim 2, wherein the composition further comprises an additional therapeutic agent.

4. The isolated antibody of claim 1, wherein the ghrelin transition state analog comprises a compound of the formula:

$N_1N_2X_1N_3N_4$ in which
$N_1$ is glycine,
$N_2$ is serine,
$X_1$ is

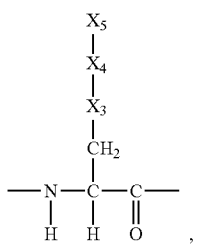

wherein $X_3$ is O or NH, $X_4$ is O=S=O or O=P—OH and $X_5$ is a hydrophobic moiety;
$N_3$ is phenylalanine, and
$N_4$ is leucine,
and wherein $N_1$ and $N_4$ each may be present or absent.

5. The isolated antibody of claim 4, wherein the hydrophobic moiety is an alkyl chain, aliphatic acid or aromatic acid.

6. The isolated antibody of claim 5, wherein the alkyl chain is a $C_6$, $C_7$, $C_8$, $C_9$ or $C_{10}$ alkyl chain.

7. The isolated antibody of claim 1, wherein the isolated antibody is an isolated single chain Fv (scFv) antibody.

8. A method of generating anti-ghrelin antibodies, comprising:
administering a ghrelin transition state analog to a subject in an amount effective to generate anti-ghrelin antibodies, and selecting for anti-ghrelin antibodies that preferentially bind the ghrelin transition state analog, cross react with octanoylated native ghrelin, and cleave octanoylated native ghrelin.

9. The method of claim 8, wherein the ghrelin transition state analog comprises a compound of the formula:

$N_1N_2X_1N_3N_4$ in which
$N_1$ is glycine,
$N_2$ is serine,
$X_1$ is

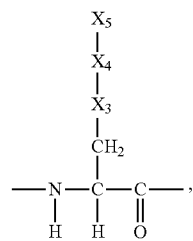

wherein $X_3$ is O or NH, $X_4$ is O=S=O or O=P—OH and $X_5$ is a hydrophobic moiety;
$N_3$ is phenylalanine, and
$N_4$ is leucine,
and wherein $N_1$ and $N_4$ each may be present or absent.

10. The method of claim 9, wherein the hydrophobic moiety is an alkyl chain, aliphatic acid or aromatic acid.

11. The method of claim 10, wherein the alkyl chain is a $C_6$, $C_7$, $C_8$, $C_9$ or $C_{10}$ alkyl chain.

12. The method of claim 8, wherein the method further comprises administering an adjuvant to the subject.

* * * * *

SEQUENCE LISTING

```
<160> NUMBER OF SEQ ID NOS: 27

<210> SEQ ID NO 1
<211> LENGTH: 28
<212> TYPE: PRT
<213> ORGANISM: Homo sapiens
<220> FEATURE:
<221> NAME/KEY: MOD_RES
<222> LOCATION: (3)..(3)
<223> OTHER INFORMATION: Octanoylation (Acylation)

<400> SEQUENCE: 1

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 2
<211> LENGTH: 28
<212> TYPE: PRT
<213> ORGANISM: Homo sapiens

<400> SEQUENCE: 2

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 3
<211> LENGTH: 4
```

-continued

```
<212> TYPE: PRT
<213> ORGANISM: Homo sapiens

<400> SEQUENCE: 3

Leu Ser Pro Glu
1

<210> SEQ ID NO 4
<211> LENGTH: 5
<212> TYPE: PRT
<213> ORGANISM: Homo sapiens

<400> SEQUENCE: 4

Leu Ser Pro Glu His
1               5

<210> SEQ ID NO 5
<211> LENGTH: 6
<212> TYPE: PRT
<213> ORGANISM: Homo sapiens

<400> SEQUENCE: 5

Leu Ser Pro Glu His Gln
1               5

<210> SEQ ID NO 6
<211> LENGTH: 7
<212> TYPE: PRT
<213> ORGANISM: Homo sapiens

<400> SEQUENCE: 6

Leu Ser Pro Glu His Gln Arg
1               5

<210> SEQ ID NO 7
<211> LENGTH: 8
<212> TYPE: PRT
<213> ORGANISM: Homo sapiens

<400> SEQUENCE: 7

Leu Ser Pro Glu His Gln Arg Val
1               5

<210> SEQ ID NO 8
<211> LENGTH: 9
<212> TYPE: PRT
<213> ORGANISM: Homo sapiens

<400> SEQUENCE: 8

Leu Ser Pro Glu His Gln Arg Val Gln
1               5

<210> SEQ ID NO 9
<211> LENGTH: 10
<212> TYPE: PRT
<213> ORGANISM: Homo sapiens

<400> SEQUENCE: 9

Leu Ser Pro Glu His Gln Arg Val Gln Gln
1               5                   10

<210> SEQ ID NO 10
<211> LENGTH: 11
<212> TYPE: PRT
<213> ORGANISM: Homo sapiens
```

```
<400> SEQUENCE: 10

Leu Ser Pro Glu His Gln Arg Val Gln Gln Arg
1               5                   10

<210> SEQ ID NO 11
<211> LENGTH: 12
<212> TYPE: PRT
<213> ORGANISM: Homo sapiens

<400> SEQUENCE: 11

Leu Ser Pro Glu His Gln Arg Val Gln Gln Arg Lys
1               5                   10

<210> SEQ ID NO 12
<211> LENGTH: 13
<212> TYPE: PRT
<213> ORGANISM: Homo sapiens

<400> SEQUENCE: 12

Leu Ser Pro Glu His Gln Arg Val Gln Gln Arg Lys Glu
1               5                   10

<210> SEQ ID NO 13
<211> LENGTH: 14
<212> TYPE: PRT
<213> ORGANISM: Homo sapiens

<400> SEQUENCE: 13

Leu Ser Pro Glu His Gln Arg Val Gln Gln Arg Lys Glu Ser
1               5                   10

<210> SEQ ID NO 14
<211> LENGTH: 15
<212> TYPE: PRT
<213> ORGANISM: Homo sapiens

<400> SEQUENCE: 14

Leu Ser Pro Glu His Gln Arg Val Gln Gln Arg Lys Glu Ser Lys
1               5                   10                  15

<210> SEQ ID NO 15
<211> LENGTH: 16
<212> TYPE: PRT
<213> ORGANISM: Homo sapiens

<400> SEQUENCE: 15

Leu Ser Pro Glu His Gln Arg Val Gln Gln Arg Lys Glu Ser Lys Lys
1               5                   10                  15

<210> SEQ ID NO 16
<211> LENGTH: 17
<212> TYPE: PRT
<213> ORGANISM: Homo sapiens

<400> SEQUENCE: 16

Leu Ser Pro Glu His Gln Arg Val Gln Gln Arg Lys Glu Ser Lys Lys
1               5                   10                  15

Pro

<210> SEQ ID NO 17
<211> LENGTH: 18
<212> TYPE: PRT
<213> ORGANISM: Homo sapiens
```

```
<400> SEQUENCE: 17

Leu Ser Pro Glu His Gln Arg Val Gln Gln Arg Lys Glu Ser Lys Lys
1               5                   10                  15

Pro Pro

<210> SEQ ID NO 18
<211> LENGTH: 19
<212> TYPE: PRT
<213> ORGANISM: Homo sapiens

<400> SEQUENCE: 18

Leu Ser Pro Glu His Gln Arg Val Gln Gln Arg Lys Glu Ser Lys Lys
1               5                   10                  15

Pro Pro Ala

<210> SEQ ID NO 19
<211> LENGTH: 20
<212> TYPE: PRT
<213> ORGANISM: Homo sapiens

<400> SEQUENCE: 19

Leu Ser Pro Glu His Gln Arg Val Gln Gln Arg Lys Glu Ser Lys Lys
1               5                   10                  15

Pro Pro Ala Lys
            20

<210> SEQ ID NO 20
<211> LENGTH: 21
<212> TYPE: PRT
<213> ORGANISM: Homo sapiens

<400> SEQUENCE: 20

Leu Ser Pro Glu His Gln Arg Val Gln Gln Arg Lys Glu Ser Lys Lys
1               5                   10                  15

Pro Pro Ala Lys Leu
            20

<210> SEQ ID NO 21
<211> LENGTH: 22
<212> TYPE: PRT
<213> ORGANISM: Homo sapiens

<400> SEQUENCE: 21

Leu Ser Pro Glu His Gln Arg Val Gln Gln Arg Lys Glu Ser Lys Lys
1               5                   10                  15

Pro Pro Ala Lys Leu Gln
            20

<210> SEQ ID NO 22
<211> LENGTH: 23
<212> TYPE: PRT
<213> ORGANISM: Homo sapiens

<400> SEQUENCE: 22

Leu Ser Pro Glu His Gln Arg Val Gln Gln Arg Lys Glu Ser Lys Lys
1               5                   10                  15

Pro Pro Ala Lys Leu Gln Pro
            20

<210> SEQ ID NO 23
```

```
<211> LENGTH: 24
<212> TYPE: PRT
<213> ORGANISM: Homo sapiens

<400> SEQUENCE: 23

Leu Ser Pro Glu His Gln Arg Val Gln Gln Arg Lys Glu Ser Lys Lys
1               5                   10                  15

Pro Pro Ala Lys Leu Gln Pro Arg
            20

<210> SEQ ID NO 24
<211> LENGTH: 5
<212> TYPE: PRT
<213> ORGANISM: Homo sapiens

<400> SEQUENCE: 24

Gly Ser Ser Phe Leu
1               5

<210> SEQ ID NO 25
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(9)
<223> OTHER INFORMATION: HA tag

<400> SEQUENCE: 25

Tyr Pro Tyr Asp Val Pro Asp Tyr Ala
1               5

<210> SEQ ID NO 26
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(5)
<223> OTHER INFORMATION: Linker

<400> SEQUENCE: 26

Gly Gly Gly Gly Ser
1               5

<210> SEQ ID NO 27
<211> LENGTH: 72
<212> TYPE: DNA
<213> ORGANISM: Artificial sequence
<220> FEATURE:
<223> OTHER INFORMATION: Synthetic polynucleotide

<400> SEQUENCE: 27
ggaggaggct cccagagact catggaggac atatgcctcc cgcgttgggg ttgtctctgg      60
gaggacgatt tt                                                         72
```